United States Patent [19]
August et al.

[11] Patent Number: 5,633,234
[45] Date of Patent: May 27, 1997

[54] LYSOSOMAL TARGETING OF IMMUNOGENS

[75] Inventors: J. Thomas August; Drew M. Pardoll; Frank G. Guarnieri, all of Baltimore, Md.

[73] Assignee: The Johns Hopkins University, Baltimore, Md.

[21] Appl. No.: 6,845

[22] Filed: Jan. 22, 1993

[51] Int. Cl.$^6$ .............................. A61K 31/70; C12N 15/62
[52] U.S. Cl. .................... 514/44; 424/185.1; 424/192.1; 435/69.3; 435/252.3; 435/320.1; 530/350; 530/395; 530/806; 536/23.4; 536/23.5
[58] Field of Search ................................ 424/18, 185.1, 424/288.1; 435/69.3

[56] References Cited

U.S. PATENT DOCUMENTS

| | | |
|---|---|---|
| 4,400,376 | 8/1983 | Sanderson . |
| 4,406,885 | 9/1983 | Pinter . |
| 4,446,128 | 5/1984 | Baschang et al. . |
| 4,448,765 | 5/1984 | Ash et al. . |
| 4,454,116 | 6/1984 | Brinton . |
| 4,578,458 | 3/1986 | Pier . |
| 4,593,002 | 6/1986 | Dulbecco . |
| 4,681,762 | 7/1987 | Oeschger et al. . |
| 4,738,846 | 4/1988 | Rose et al. . |
| 4,769,330 | 9/1988 | Paoletti . |
| 4,920,209 | 4/1990 | Davis et al. . |

FOREIGN PATENT DOCUMENTS

| | | |
|---|---|---|
| WO 92/18150 | 10/1992 | WIPO . |
| WO 93/06216 | 4/1993 | WIPO . |

OTHER PUBLICATIONS

Paul, W.E. Fundamental Immunology 2nd Edition see pp. 188–190 and 936 1989.
Tizard, I. An Introduction to Veterinary Immunology see p. 253 1982.
Inaba et al. J. Exp. Med. 172:631–640 Aug. 1990.
Scheicher et al. J. Immunol. Methods 154:253–264 1992.
Peters, et al., "Targeting of a Lysosomal Membrane Protein: A Tyrosine–Containing Endocytosis Signal in the Cytoplasmic Tail of Lysosomal Acid Phosphatase is Necessary and Sufficient for Targeting to Lysosomes," *EMBO Journal*, 9:3497–3506 (1990).
Harding, et al., "Liposome–Encapsulated Antigens Are Processed in Lysosomes, Recycled , and Presented to T Cells," *Cell*, 64:393–401 (1991).
Sanger, et al., "DNA Sequencing With Chain–Terminating Inhibitors," Proc. Nat. Acad. Sci. U.S.A., 74:5463–5467 (1977).
Hughes, et al., "Murine Fibroblast Plasma Membrane Proteins Identified by Monoclonal Antibodies. In: Leukaemias, Lymphomas and Papillomas: Comparative Aspects," pp. 65–86 (1980) P. A. Bachmann (ed.). Taylor and Francis Ltd., London.
Hughes, et al., "Characterization of Plasma Membrane Proteins Identified by Monoclonal Antibodies," J. Biol. Chem., 256:664–671 (1981).

Mengod, et al., "Murine Cell Surface Glycoproteins: Immunochemical Analysis of a Major Differentiation Alloantigen of Phagocytotic Cells," Arch. Biochem. Biophys., 209:718–722 (1981).
Hughes, et al., "Murine Cell Surface Glycoproteins: Identification, Purification, and Characterization of a Major Glycosylated Component of 110,000 Daltons by Use of a Monoclonal Antibody," J. Biol. Chem., 257:3970–3977 (1982).
Hughes, et al., "Murine Cell Surface Glycoproteins: Purification of the Polymorphic Pgp–1 Antigen and Analysis of its Expression on Macrophages and Other Myeloid Cells," J. Biol. Chem., 258:1014–1021 (1983).
Chen, et al., "Lysosome–Associated Membrane Proteins: Characterization of LAMP-1 of Macrophage P388 and Mouse Embryo 3T3 Cultured Cells," Arch Biochem. Biophys., 239:574–586 (1985).
Chen, et al., "Identification of Two Lysosomal Membrane Glycoproteins," J. Cell Biol., 101:85–95 (1985).
Lewis, et al., "Glycoproteins of the Lysosomal Membrane," J. Cell Biol., 100:1839–1847 (1985).
Taylor, et al., "The Use of Phosphorothioate–Modified DNA in Restriction Enzyme Reactions to Prepare Nicked DNA" Nucl. Acids Res., 13:8749–8764 (1985).
Taylor, et al., "The Rapid Generation of Oligonucleotide–Directed Mutations at a High Frequency Using Phosphorothioate–Modified DNA," Nucl. Acids Res., 13:8765–8785 (1985).
Chen, et al., "Lysosomal Membrane Glycoproteins: Properties of LAMP-1 and LAMP-2," Biochem. Soc. Symp., 51:97–112 (1986).
Lippincott–Schwartz, et al., "Lysosomal Membrane Dynamics: Structure And Interorganellar Movement of a Major Lysosomal Membrane Glycoprotein," J. Cell Biol., 102:1593–1605 (1986).

(List continued on next page.)

*Primary Examiner*—Thomas M. Cunningham
*Attorney, Agent, or Firm*—Banner & Witcoff, Ltd.

[57] ABSTRACT

The inventors have discovered a targeting signal that will direct proteins to the endosomal/lysosomal compartment, and they have demonstrated that chimeric proteins containing a luminal antigenic domain and a cytoplasmic endosomal/lysosomal targeting signal will effectively target antigens to that compartment, where the antigenic domain is processed and peptides from it are presented on the cell surface in association with major histocompatibility (MHC) class II molecules. Chimeric DNA encoding the antigen of interest, linked to an endosomal/lysosomal targeting sequence, inserted in an immunization vector, can introduce the chimeric genes into cells, where the recombinant antigens are expressed and targeted to the endosomal/lysosomal compartment. As a result, the antigens associate more efficiently with MHC class II molecules, providing enhanced in vivo stimulation of CD4$^+$ T cells specific for the recombinant antigen. Delivering antigens to an endosomal/lysosomal compartment by means of chimeric constructs containing such lysosomal targeting signals will be of value in any vaccination or immunization strategy that seeks to stimulate CD4$^+$ MHC class II restricted immune responses.

20 Claims, 4 Drawing Sheets

OTHER PUBLICATIONS

Barriocanal, et al., "Biosynthesis, Glycosylation, Movement Through the Golgi System, and Transport To Lysosomes By an N–Linked Carbohydrate–Independent Mechanism of Three Lysosomal Integral Membrane Proteins," J. Biol. Chem., 261:16755–16763 (1986).

Nakamaye, et al., "Inhibition of Restriction Endonuclease Nci I Cleavage by Phosphorothioate Groups and its Application to Oligonucleotide–Directed Mutagenesis," Nucl. Acids Res., 14:9679–9698 (1986).

D'Souza, et al., "A Kinetic Analysis of Biosynthesis and Localization of a Lysosome–Associated Membrane Glycoprotein," Arch. Biochem. Biophys., 249:522–532 (1986).

Lippincott–Schwartz, et al., "Cycling of the Integral Membrane Glycoprotein, LEP100, Between Plasma Membrane and Lysosomes: Kinetic and Morphological Analysis," Cell, 49:669–677 (1987).

Green, et al., "Kinetics of Intracellular Transport and Sorting of Lysosomal Membrane and Plasma Membrane Proteins," J. Cell Biol., 105:1227–1240 (1987).

Fambrough, et al., "Structure of LEP100, a Glycoprotein that Shuttles Between Lysosomes and the Plasma Membrane, Deduced from the Nucleotide Sequence of the Encoding cDNA," J. Cell. Biol., 106:61–67 (1988).

Sayers, et al., "5'–3' Exonucleases in Phosphorothioate–Based Oligonucleotide–Directed Mutagenesis," Nucl. Acids Res., 16:791–802 (1988).

Goldenthal, et al., "Pre–lysosomal Divergence of Alpha$_2$–Macroglobulin and Transferrin: A Kinetic Study Using a Monoclonal Antibody Against a Lysosomal Membrane Glycoprotein (LAMP–1)," J. Histochem. and Cytochem., 36:391–400 (1988).

Hotta, H., et al., "Molecular Cloning and Characterization of An Antigen Associated with Early Stages of Melanoma Tumor Progression," Cancer Res., 48:2955–2962 (1988).

Chen, et al., "Isolation and Sequencing of a cDNA Clone Encoding Lysosomal Membrane Glycoprotein Mouse LAMP–1: Sequence Similarity to Proteins Bearing Onco–Differentiation Antigens," J. Biol. Chem., 263:8754–8758 (1988).

Carlsson, et al., "Isolation and Characterization of Human Lysosomal Membrane Glycoproteins, h–LAMP–1 and h–LAMP–2: Major Sialoglycoproteins Carrying Polylactosaminoglycan," J. Biol. Chem., 263:18911–18919 (1988).

Fukuda, et al., "Cloning of cDNAs Encoding Human Lysosomal Membrane Glycoproteins, h–LAMP–1 and h–LAMP–2: Comparison of Their Deduced Amino Acid Sequences," J. Biol. Chem., 263:18920–18928 (1988).

Arterburn, et al., "Biosynthesis and Processing of Lysosomal Membrane Glycoproteins," In: Intracellular Trafficking of Proteins, pp. 472–503 (1989) (C.J. Steer and J.A. Hanover, Eds.) Cambridge University Press, England.

Sandoval, et al., "Lysosomal Integral Membrane Glycoproteins are Expressed at High Levels in the Inclusion Bodies of I–Cell Disease Fibroblasts," Arch. Biochem. Biophys., 271:1–11 (1989).

Kornfield, et al., "The Biogenesis of Lysosomes," Annu. Rev. Cell Biol., 5:483–525 (1989).

Gottschalk, et al., "Sequential Processing of Lysosomal Acid Phosphatase by a Cytoplasmic Thiol Proteinase and a Lysosomal Aspartyl Proteinase," EMBO J., 8:3215–3219 (1989).

Wolffe, et al., "The cDNA Sequence of Mouse Pgp–1 and Homology to Human CD44 Cell Surface Antigen and Proteoglycan Core/Link Proteins," J. Biol. Chem., 265:341–347 (1990).

Chen, et al., "NPXY, A Sequence Often Found in Cytoplasmic Tails, is Required for Coated Pit–Mediated Internalization of the Low Density Lipoprotein Receptor," J. Biol. Chem., 265:3116–3123 (1990).

Cha, et al., "The cDNA Sequence of Mouse LAMP–2," J. Biol. Chem.,265:5008–5013 (1990).

Arterburn, et al., "The Disulfide Structure of Mouse Lysosome–Associated Membrane Protein 1," J. Biol. Chem., 265:7419–7423 (1990).

Metzelaar, et al., "CD63 Antigen: A Novel Lysosomal Membrane Glycoprotein, Cloned By a Screening Procedure for Intracellular Antigens in Eukaryotic Cells," J. Biol. Chem., 266:3239–3245 (1991).

Azorsa, et al., "CD63/Pltgp 40: A Platelet Activation Antigen Identical to the Stage–Specific, Melanoma–Associated Antigen ME491," Blood, 78:280–284 (1991).

Horejsi, et al., "Novel Structurally Distinct Family of Leucocyte Surface Glycoproteins Including CD9, CD37, CD53 and CD63," FEBS Lett., 288:1–4 (1991).

Vega, et al., "Cloning, Sequencing, and Expression of a cDNA Encoding Rat LIMP II, a Novel 74–kDa Lysosomal Membrane Protein Related to the Surface Adhesion Protein CD36," J. Biol. Chem., 266:16818–16824 (1991).

Harter, et al., "Transport of the Lysosomal Membrane Glycoprotein lgp120 (lgp–A) to Lysosomes Does Not Require Appearance on the Plasma Membrane," J. Cell Biol., 117:311–325 (1992).

Harding et al. J. Immurology 147(9):2860–63 1991.

Jadot, et al., (1992) "Characterization of the Signal for Rapid Internalization of the Bovine Mannose 6–Phosphate/Insulin–Like Growth Factor–II Reeptor", J. Biol. Chem., 267:11069–11077.

Vega, et al., (1991) "Targeting of Lysosomal Integral Membrane Protein LIMPII", J. Biol. Chem., 266:16269–16272.

Breitfield, et al., (1990) "Deletions in the Cytoplasmic Domain of the Polymeric Immunoglobulin Receptor Differentially Affect Endocytotic Rate and Postendocytotic Traffic", J. Biol. Chem., 265:13750–13757.

Canfield, et al., (1991) "Localization of the Signal for Rapid Internalization of the Bovine Cation–Independent Mannose 6–Phosphate/Insulin–Like Growth Factor–II Receptor to Amino Acids 24–29 of the Cytoplasmic Tail", J. Biol. Chem., 266:5682–5688.

Collawn, et al., (1990) "Transferrin Receptor Internalization Sequence YXRF Implicates a Tight Turn as the Structural Recognition Motif for Endocytosis", Cell., 63:1061–1072.

Johnson, et al., (1990) "Cation–Dependent Mannose 6–Phosphate Receptor Contains Two Internalization Signals in its Cytoplasmic Domain", Proc. Natl. Acad. Sci. U.S.A., 87:10010–10014.

Peters, et al., (1990) "Targeting of a Lysosomal Membrane Protein: a Tyrosine–Containing Endocytosis Signal in the Cytoplasmic Tail of Lysosomal Acid Phosphatase is Necessary and Sufficient for Targeting to Lysosomes", EMBO J., 9:3497–3506.

Williams, et al., (1990) "Accumulation of Membrane Glycoproteins in Lysosomes Requires a Tyrosine Residue at a Particular Position in the Cytoplasmic Tail", J. Cell. Biol., 111:955–966.

Mane, et al., (1989) "Purification and Characterization of Human Lysosomal Membrane Glycoproteins", Archiv. Biochem. Biophys., 268:360–378.

Pohlmann, et al., (1988) "Human Lysosomal Acid Phosphatase: Cloning, Expression, and Chromosomal Assignment", EMBO J., 7:2343–2350.

FIG. IA
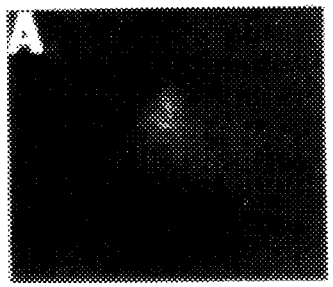
FIG. IE
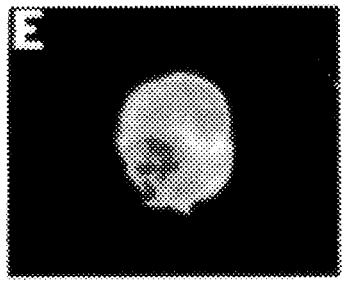
FIG. II
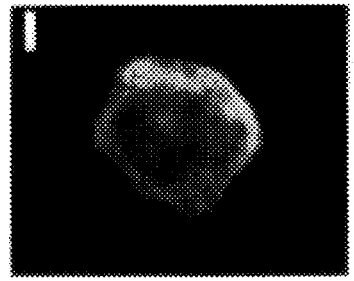
FIG. IB
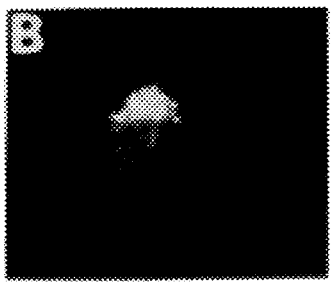
FIG. IF
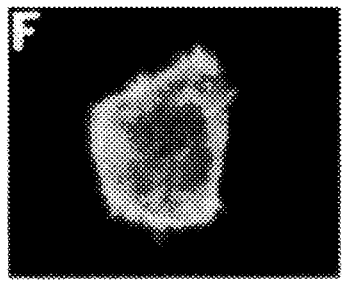
FIG. IJ
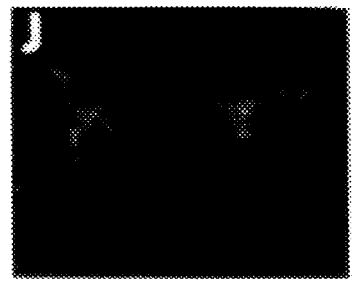
FIG. IC
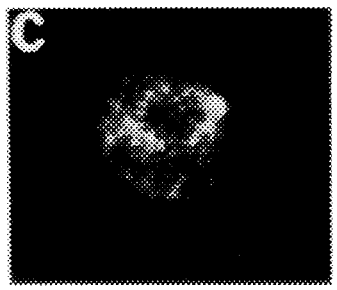
FIG. IG
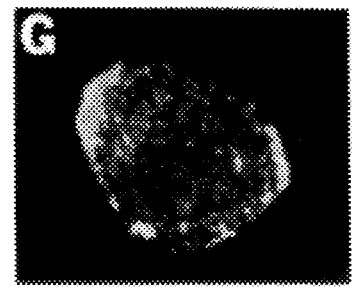
FIG. IK
FIG. ID
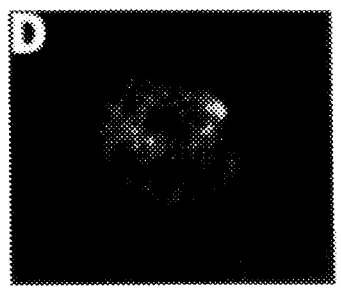
FIG. IH
FIG. IL

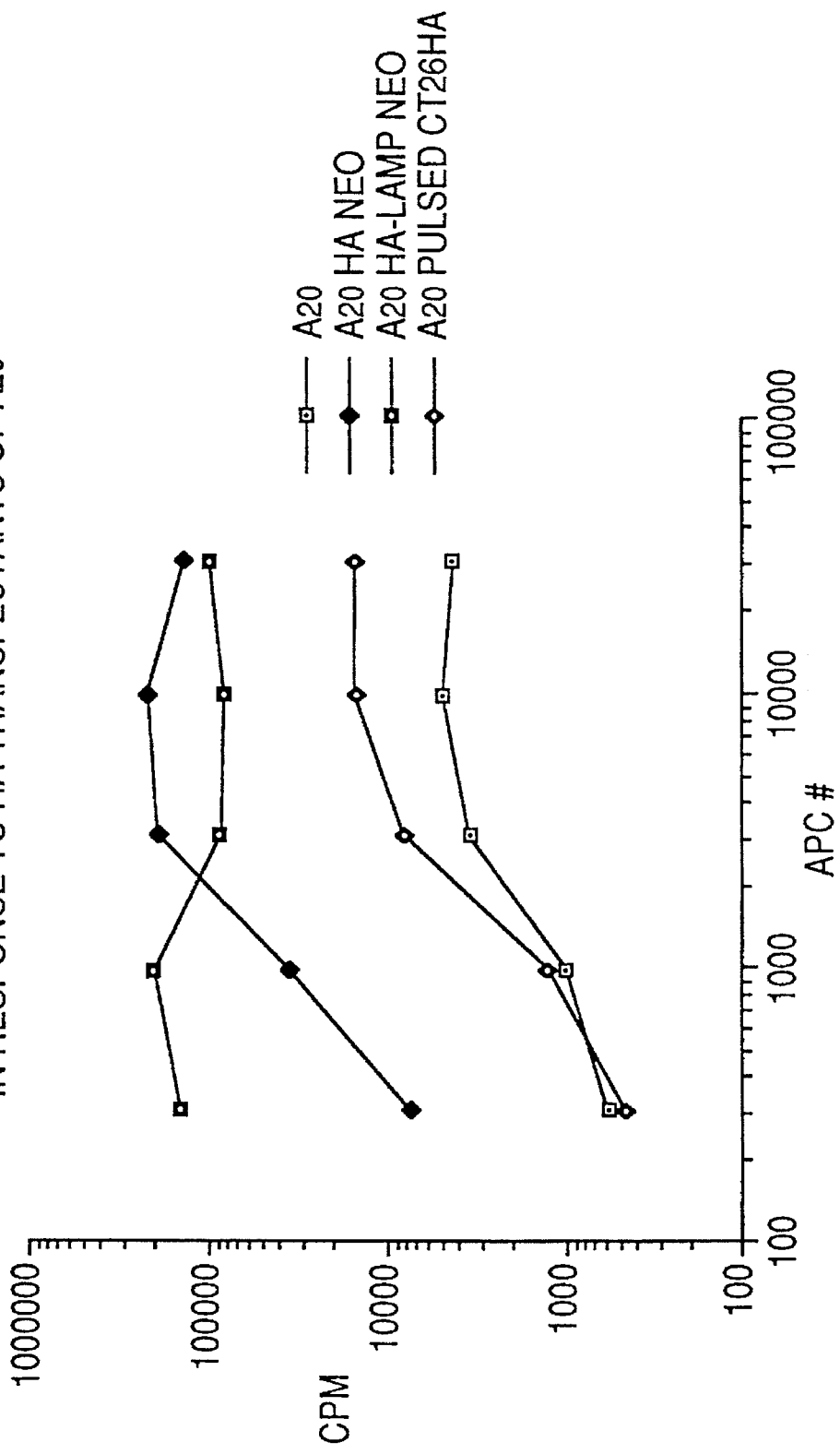

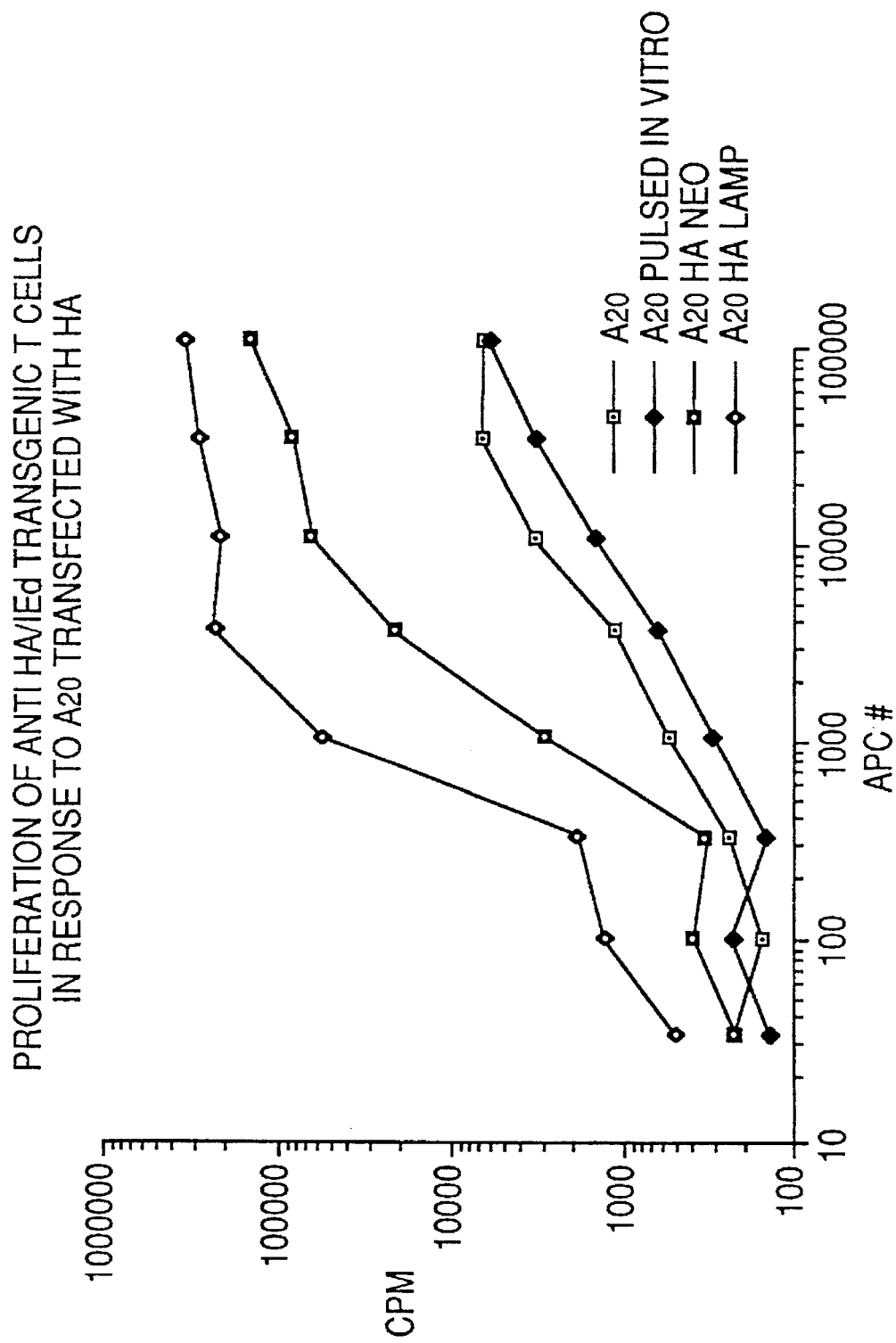

LYSOSOMAL TARGETING OF IMMUNOGENS

The work leading to this invention was supported in part by Grant No. NOI-HD-62915 from the National Institutes of Health. The United States Government may retain certain rights in this invention.

BACKGROUND OF THE INVENTION

1. Field of the Invention

This invention relates generally to the introduction into proteins of amino acid segments having a biological targeting function which directs the proteins to cellular vesicles where they are processed into peptide residues recognized by the major histocompatibility complex class II proteins and to the use of this procedure to enhance the immune response of mammals to these targeted proteins as antigens.

2. Review of Related Art

A. Antigen Processing and Presentation to T Cells

The generally held theory for the mechanism of antigen recognition and response in the mammalian immune system is that there are two parallel cellular systems of T cells and antigen presenting molecules which distinguish between two types of antigens, foreign antigens introduced from outside of the cell (such as foreign chemicals, bacteria, and toxins) and endogenous antigens produced within the cell (such as viruses or oncogene products). It is now clear that the cell type which distinguishes between antigen types in the cellular immune response is the T cell. Via its heterodimeric T cell receptor, the T cell recognizes peptide fragments of these antigens presented as a complex with major histocompatibility (MHC) molecules (Yewdell and Bennenk, *Cell*, 62:203, 1990; Davis and Bjorkman, *Nature*, 334:395, 1988).

There are two general classes of MHC molecules, MHC class I and MHC class II proteins. These MHC molecules bind to antigens and present them to one of the two types of the T cell class of white blood cells, cytotoxic T cells ($T_c$) or helper T cells ($T_h$). MHC class I molecules present peptide antigens generally derived from endogenously produced proteins to the $CD8^+T_c$ cells, the predominant cytotoxic T cell that is antigen specific. MHC class II molecules generally present antigens that are introduced from without the cells, utilizing a distinct pathway for antigen presentation that involves generation of peptide fragments in endosomal/lysosomal organelles. MHC class II molecules are also found in these acidic organelles, co-localized with the invariant chain, a membrane glycoprotein that binds MHC class II proteins in the endoplasmic reticulum and is replaced by the antigenic peptides. After binding of the antigen to the class II molecules, the antigen/MHC II complex is brought to the cell surface for antigen presentation to $CD4^+$ $T_h$ cells.

The functions of the two types of T cells are significantly different, as implied by their names. Cytotoxic T cells act to eradicate intracellular pathogens and tumors by direct lysis of cells and by secreting cytokines such a γ-interferon. Helper T cells can also lyse cells, but their primary function is to secrete cytokines that promote the activities of B cells and other T cells and thus they broadly enhance the immune response to foreign antigens, including antibody-mediated and $T_c$-mediated response mechanisms.

$CD4^+$T cells are the major helper T cell phenotype in the immune response. Their predominant function is to generate cytokines which regulate essentially all other functions of the immune response. Animals depleted of $CD4^+$ or humans depleted of $CD4^+$ cells (as in patients with AIDS) fail to generate antibody responses, cytotoxic T cell responses, or delayed type hypersensitivity responses. These results suggest that helper T cells are critical in regulating immune responses.

$CD4^+$MHC class II restricted cells have also been shown to have cytotoxic capacity in a number of systems. One of the most important disease-relevant cases in which $CD4^+$ cytotoxic T cells have been demonstrated is in the response to fragments of the HIV gp120 protein (Polydefkis, et al., *J. Exp. Med.*, 171:875, 1990). $CD4^+$MHC class II restricted cells have also been shown to be critical in generating systemic immune responses against tumors. In an adoptive transfer model, $CD4^+$ cells are critical in eliminating FBL tumors in mice. In the active immunotherapy model of Golumbek, et al. (1991, *Science*, 254:713), $CD4^+$ cells have also been shown to be critical in the systemic immune response against a number of different solid malignancies.

For all these reasons there has been increased interest in developing strategies that will most effectively activate MHC class II restricted $CD4^+$ cells against a given specific antigen. Furthermore, $CD4^+$MHC class II restricted cells appear to be the critical memory cells in the T cell arm of the immune response. Therefore, an appropriate vaccination strategy is to generate $CD4^+$ antigen-specific MHC class II-restricted memory T cell populations.

In keeping with the different functions of the cytolytic T cells and helper T cells, the tissue distribution of the MHC molecules that present antigens to these cells is markedly different. The MHC I protein complex that recognizes self or viral antigens is found in virtually all cell types, whereas the MHC II protein that reacts with foreign antigens is found largely in immune cells such as macrophages and macrophage-like cells that either secrete cytokines necessary for $T_h$ cell stimulation of B cells or that require the $T_h$ cell cytokines for their own stimulation. Cells exhibiting MHC II protein are generally called antigen presenting cells.

The processing and presentation of self or foreign antigens to the MHC I or MHC II complex, respectively, generally occurs in different pathways (Bevan, *Nature*, 325:192, 1987; Braciale, et al., *Immunol. Rev.*, 98:95, 1987; Germain, *Nature*, 322:687, 1986):

(1) The MHC class I-related proteolytic system is present in virtually all cells for the purpose of degrading highly abnormal proteins and short-lived molecules or viral proteins. This proteolysis is thought to be non-lysosomal and to involve ATP-dependent covalent conjugation to the polypeptide ubiquitin (Goldberg, et al., *Nature*, 357:375, 1992). Peptide fragments, possibly in association with a larger proteasome complex, are then postulated to enter into the endoplasmic reticulum or some other type of exocytic compartment (other than the endocytic/lysosomal compartment). There they bind to MHC class I molecules and follow the constitutive secretary pathway from the endoplasmic reticulum through the Golgi to the cell surface where they are presented by the MHC I protein to the CD3–CD8 cytotoxic T cell antigen receptor.

(2) The MHC class II-related process by which foreign antigens are processed in antigen presenting cells (APC) cells is generally believed to occur in an endocytic pathway. Antigens taken into the cell by fluid-phase pinocytosis, absorptive endocytosis, or phagocytosis enter into a late endosomal/lysosomal compartment where large molecules are converted to peptides by digestion through proteases and other hydrolases. During this process, the immunodominant smaller peptides come in contact with and are bound by MHC class II molecules and the peptides are carried to the cell surface. On the cell surface of APC, these short peptides in conjunction with MHC class II molecules bind the CD3–CD4 complex on the surface of helper T cells, activating the replication and immune function of these cells. Following this interaction, helper T cells release lymphokines that stimulate the proliferation and differentiation of leukocytes and inhibit their emigration from the site of infection. In general, the activation of helper T cells by peptide-loaded APC is required for optimal B cell and T cell action, and thus is necessary for proper immune system function.

Some endogenous proteins may also enter the MHC class II system for antigen presentation (Malnati, et al., *Nature*, 357:702, 1992; Polydefkis, et al., 1990). It is postulated that endogenously-produced membrane antigen, which remains attached to the luminal/extracellular membrane by a hydrophobic anchor sequence, can recycle to the endosomal/lysosomal compartment by first reaching the surface of the cell via bulk flow followed by endocytic uptake and subsequent processing by the normal class II pathway for processing of exogenous antigens. MHC class II molecules may also present some antigenic determinants derived from endogenous proteins that are sequestered in the endoplasmic reticulum or other compartments and are then processed in salvage pathways to the lysosome (Brooks, et al., *Proc. Nat'l. Acad. Sci. USA*, 88:3290, 1991).

Other possible processing pathways for presentation of endogenously derived or cytosolic proteins to MHC class II-restricted T cells have also been described in some but not all experimental systems. These appear to be less efficient that the class I-associated process, and are not well understood (Moreno, et al., *J. Immunol.*, 147:3306, 1991; Jaraquemada, et al., *J. Exp. Med.*, 172:947, 1990). Alternative types of antigen presenting cells with different pathways for protein processing have been suggested, as well as the possibility of different proteases. The antigen-presenting capacity of cells bearing MHC class II shows variation according to cell type and is likely to be related to the proteolytic machinery and intracellular routes followed by antigen and MHC class II molecules (Peters, et al., *Nature*, 349:669, 1991).

The exact site of antigen processing and association of processed peptides with MHC class II in the endosomal/lysosomal pathway is as yet unclear. Data have been presented suggesting that MHC class II molecules meet with endocytosed proteins in the early endosomal compartment (Guagliardi, et al., *Nature*, 343:133, 1990). Partially processed antigens and easily degradable antigens may yield peptides that can combine with MHC class II in the early endosomal compartment. However, evidence is mounting that the major site of antigen processing and association with MHC class II occurs either in the late endosome, the lysosome, or a distinct compartment related to the lysosome (Neefjes, et al., *Cell*, 61:171, 1990). Recent studies describe a distinct vesicular compartment with lysosomal properties and characterized by high concentration of lysosomal-associated membrane protein (LAMP-1) and MHC class II molecules (Peters, et al., 1991).

The available data suggest the following sequence of events in the intracellular transport of MHC class II molecules: MHC class II molecules with the invariant chain are assembled in the endoplasmic reticulum and transported through the Golgi in common with other membrane proteins including MHC class I. The molecules are then targeted to specific endosomal/lysosomal organelles by an unknown mechanism, segregating from the MHC class I molecules which follow a constitutive route to the cell surface. In the endocytotic/lysosomal route, the invariant chain is removed from MHC class II by proteases acting in an acidic environment. At the same time, antigenic fragments of proteins that have entered the endocytic/lysosomal pathway are generated by these proteases and the resulting peptides bind to the class II molecules and are carried to the cell surface.

B. Lysosomal/Endosomal Compartment

As described herein, the lysosomal/endosomal compartment is composed of membrane-bound acidic vacuoles containing LAMP molecules in the membrane, hydrolytic enzymes that function in antigen processing, and MHC class II molecules for antigen recognition and presentation. This compartment functions as a site for degradation of foreign materials internalized from the cell surface by any of a variety of mechanisms including endocytosis, phagocytosis and pinocytosis, and of intracellular material delivered to this compartment by specialized autolytic phenomena (de Duve, *Eur. J. Biochem.*, 137:391, 1983).

The biosynthesis and vacuolar targeting mechanisms of the hydrolytic enzymes present in the lysosomal/endosomal compartment have been extensively studied (Kornfeld & Mellman, *Ann. Rev. Cell Biol.*, 5:483, 1989). Newly synthesized hydrolases in the Golgi apparatus acquire mannose 6-phosphate groups that serve as specific recognition markers for the binding of these enzymes to mannose 6-phosphate receptors which are then targeted in some unknown manner to a prelysosomal vacuole. There the receptor-enzyme complex is dissociated by low pH, and the receptors recycle to the Golgi apparatus, while the enzyme-containing vacuole matures into a lysosome.

Studies of the structure and function of the lysosomal membrane were initiated in 1981 by August and colleagues with the discovery of major cellular glycoproteins that were subsequently termed lysosomal-associated membrane proteins one and two (LAMP-1 and LAMP-2) due to their predominant localization in the lysosomal membrane (Hughes, et al., *J. Biol. Chem.*, 256:664, 1981; Chen, et al., *J. Cell Biol.*, 101:85, 1985). Analogous proteins were subsequently identified in rat, chicken and human cells (Barriocanal, et al., *J. Biol. Chem.*, 261:16755, 1986; Lewis, et al., *J. Cell Biol.*, 100:1839, 1985; Fambourgh, et al., *J. Cell Biol.*, 106:61, 1988; Mane, et al., *Arch. Biochem. Biophys.*, 268:360, 1989). Typically, LAMP-1, as deduced from a cDNA clone (Chen, et al., *J. Biol. Chem.*, 263:8754, 1988) consists of a polypeptide core of about 382 amino acids ($Mr \approx 42,000$) with a large (346-residue) intraluminal amino-terminal domain followed by a 24-residue hydrophobic transmembrane region and short (12-residue) carboxyl-terminal cytoplasmic tail. The intraluminal domain is highly glycosylated, being substituted with about 20 asparagine linked complex-type oligosaccharides and consists of two ~160-residue homology units that are separated by a proline/serine-rich region. Each of these homologous domains contains 4 uniformly spaced cysteine residues, disulfide bonded to form four 36–38-residue loops symmetrically placed within the two halves of the intraluminal domain (Arterburn, et al., *J. Biol. Chem.*, 265:7419, 1990, see especially FIG. 6). The LAMP-2 molecule is highly similar to LAMP-1 in overall amino acid sequence (Cha, et al., *J. Biol. Chem.*, 265:5008, 1990).

Another glycoprotein, described as CD63, MEA491 or LIMP 1, is also found in lysosomal membranes, as well as other in vacuolar structures (Azorza, et al., *Blood*, 78:280, 1991). This molecule is distinctly different from the LAMPs, with a core polypeptide of about 25,000 kDa and four transmembrane domains, but it has a cytoplasmic structure and sequence similar the LAMP molecules. There is also extensive amino acid sequence similarity between this protein and a family of other molecules that also contain four membrane spanning domains, including the *Schistosoma mansoni* membrane protein SM23, CD37, the tumor-associated antigen CO-029, and the target of an antiproliferative antibody-1.

Lysosomal acid phosphatase (LAP) is a hydrolytic enzyme that is also initially present in the lysosomal membrane, where it is subject to limited proteolysis that generates the soluble mature enzyme (Peters, et al., *EMBO J.*, 9:3497, 1990). The protein has little sequence homology to the other described lysosomal membrane components, but it does contain a targeting sequence in the 19 residue cytoplasmic tail of the molecule (Pohlmann, et al., *EMBO J.*, 7:2343, 1988).

LIMP II is an additional glycoprotein present in the membrane of lysosomes and secretory granules with lysosomal properties (Vega, et al., *J. Biol. Chem.*, 266:16818, 1991). A sequence near the amino-terminus with properties of an uncleavable signal peptide and a hydrophobic amine acid segment near the carboxyl end suggest that the protein is anchored in cell membranes at two sites by two short cytoplasmic tails at the amine and carboxyl-terminal ends of the protein. The molecule does not have sequence hemology to any of the other described lysosomal membrane protein, but is highly similar to the cell surface protein CD36 which is involved in cell adhesion.

C. Other Proteins Found in the Endosomal/Lysosomal Compartment

A number of other proteins have biological functions that also involve trafficking or targeting to or through vacuoles that may functionally involve the lysosomal/endosomal compartment. Examples of the most extensively characterized of these proteins at this time are as follows:

1. Cell Surface Receptors:

Many cell surface receptors are known whose function is to bind and carry ligands into the cell. Examples include receptors for the low density lipoprotein (LDL, Chen, et al., *J. Biol. Chem.*, 265:3116, 1990), insulin (Rajagopalam, et al., *J. Biol. Chem.*, 266:23068, 1991), epidermal growth factor (Helin and Beguinot, *J. Biol. Chem.*, 266:8363, 1991), polymeric immunoglobulin (Poly-Ig, Breitfield, et al., *J. Biol. Chem.*, 265:13750, 1990), transferring (Collawn, et al., *Cell*, 63:1061, 1990), cation-dependent and independent mannose 6-phosphate receptors (MPR, Johnson, et al., *Proc. Nat'l. Acad. Sci. USA*, 87:10010, 1990; Canfield, et al., *J. Cell Biol.*, 266:5682, 1990; Jadot, et al., *J. Biol. Chem.*, 267:11069, 1992), and CD3 (Letourneur and Klausner, *Cell*, 69:1143, 1992). Trafficking of these receptors is commonly into an endosomal, and sometimes the lysosomal compartment. A well known mechanism includes the functional dissociation of the receptor-ligand complex in the acidic environment of the endosomal/lysosomal vacuole, releasing the ligand in the cell with the subsequent recycling of the receptor to the plasma membrane.

2. Mannose 6-phosphate Receptor and Lysosomal Hydrolases:

A highly characterized mechanism for delivering hydrolytic enzymes to lysosomes is the mannose 6-phosphate receptor which specifically recognizes the mannose 6-phosphate residues selectively added to these enzymes in their biosynthetic pathway (for review see Kornfeld and Mellman, 1989). This receptor targets the hydrolysases to a committed prelysosomal compartment where the membrane-bound receptor dissociates from the soluble hydrolase, and the receptor recycles to the Golgi or to the plasma membrane while the hydrolase-containing vacuole matures into or fuses with the lysosomal vesicle marked by the presence of the LAMP molecules.

3. MHC Class II Molecule:

The MHC class II molecule is also colocalized with the LAMP proteins in the endosomal/lysosomal compartment, where it binds to peptide fragments produced from molecules processed in this compartment by proteolytic enzymes. There is evidence that the targeting signal for this localization resides in the cytoplasmic tail of the invariant chain associated with the MHC class II molecule.

4. Other Lysosomal/Endosomal Membrane Proteins:

In additional to the proteins described above as components of the endosomal/lysosomal membrane, there is evidence for the presence of a number of other lysosomal/endosomal membrane proteins to serve a variety of functions associated with the structure or function of the vesicle, such as transport molecules, receptors or specific adhesion, association or signal molecules.

D. Lysosomal/Endosomal Targeting Signals

The localization of the lysosomal membrane glycoproteins is controlled by a targeting mechanism independent of the well defined mannose 6-phosphate receptor (MPR) pathway for hydrolytic lysosomal enzymes (Kornfeld and Mellman, 1989). Kinetic analysis of intracellular transport and targeting of newly synthesized LAMP-1 and other similar proteins indicate that the molecule is synthesized in the endoplasmic reticulum, processed in the Golgi cisternae and transported to lysosomes within one hour of its biosynthesis, without detectable accumulation in the plasma membrane (Barriocanal, et al., 1986; D'Sousa, et al., *Arch. Biochem. Biophys.*, 249:522, 1986; Green, et al., *J. Cell Biol.*, 105:1227, 1987).

The eleven amino-acid sequence of the cytoplasmic tail of LAMP-1 and other similar lysosomal membrane glycoproteins has the following sequence: $Arg^{372}$-$Lys^{373}$-$Arg^{374}$-$Ser^{375}$-$His^{376}$-$Ala^{377}$-$Gly^{378}$-$Tyr^{379}$-$Gln^{380}$-$Thr^{381}$-$Ile^{382}$-COOH (Chen, et al., 1988). Studies of the signals that target these proteins to lysosomes have focused on this sequence and it was shown that $Tyr^{379}$ is critical for lysosomal targeting and that $His^{376}$, $Ala^{377}$, and $Gly^{378}$ are unimportant in the targeting of the protein (Williams and Fukuda, et al., *J. Cell Biol.*, 111:955, 1990).

A cytoplasmic Tyr is also critical for internalization from the cell surface of several receptors including low density lipoprotein (LDL) (Chen, et al., 1990), insulin (Rajagopalam, et al., 1991), epidermal growth factor (Helin and Beguinot, 1991), polymeric immunoglobulin (Poly-Ig) (Breitfield, et al., 1990), transferrin (Collawn, et al., 1990), cation-dependent and independent mannose 6-phosphate receptors (MPR) (Johnson, et al., 1990; Canfield, et al., 1990; Jadot, et al., 1992), and CD3 (Letourneur and Klausner, 1992). In the case of CD3, the molecule also utilizes a dileucine motif in the targeting mechanism.

E. Vaccine Development

Traditional vaccines rely on whole organisms, either pathogenic strains that have been killed or strains with attenuated pathogenicity. On the one hand, these vaccines run the risk of introducing the disease they are designed to prevent if the attenuation is insufficient or if enough organisms survive the killing step during vaccine preparation. On the other hand, such vaccines have reduced infectivity and are often insufficiently immunogenic, resulting in inadequate protection from the vaccination.

Recently, molecular biological techniques have been used in an attempt to develop new vaccines based on individual antigenic proteins from the pathogenic organisms. Conceptually, use of antigenic peptides rather than whole organisms would avoid pathogenicity while providing a vaccine containing the most immunogenic epitopes. However, it has been found that pure peptides or carbohydrates tend to be weak immunogens, seeming to require a chemical adjuvant in order to be properly processed and efficiently presented to the immune system. A vaccine dependent on T cell responses should contain as many T cell epitopes as would be needed to stimulate immunity in a target population of diverse MHC types. Further, since T cell recognition requires intracellular protein processing, vaccine preparations facilitating internalization and processing of antigen should generate a more effective immune response. Previous attempts to direct antigens to MHC molecules (see U.S. Pat. No. 4,400,276) were not effective because the antigen processing step was evaded. A successful hepatitis B vaccine has been prepared using cloned surface antigen of the hepatitis B virus, but this appears to be due to the tendency of the hepatitis surface antigen molecule to aggregate, forming regular particles that are highly immunogenic.

F. Cancer Vaccines

It is now well known that tumors express antigens that are capable of being recognized as foreign from host antigens by the T cell arm of the immune system and there are many potential types of tumor specific antigens:

* EBV Epstein-Barr virus gene products in Hodgkin's lymphomas as well as Burkits and other lymphomas, products of the HTLV-1 genome in adult T cell leukemia and human papillomavirus (HPV) E6 and E7 gene products in cervical carcinoma.
* Mutations in various oncogenes such as the position 12 mutation in K ras have been implicated as a major genetic alteration of colon cancer as well as other malignancies.
* Mutations in tumor suppressor genes such as P53 are extremely common in many malignancies.
* Rearrangements that result in activation of oncogenes such as the rearrangement between the BCR and abl gene in chronic myelogenous leukemia generate notel protein sequences.
* Tumors re-express developmental or embryonic genes which are not expressed in normal cells in the individual. Such an example is the MAGE gene identified as a source of a T cell recognized antigen in human melanoma.

In many cases, it has been demonstrated that peptides derived from altered genetic sequences of the sort described above can associate with either MHC class I or MHC class II molecules and be recognized by the appropriate helper or cytotoxic T cells.

The major thrust of cancer immunotherapy is the identification of these tumor specific antigens and then the development of immunization strategies that will most effectively generate T cell dependent immunity against these antigens. For example, studies indicate that vaccinia virus recombinant vaccines containing either the SV40 T antigen genes or the E6 and E7 genes from HPV or influenza nucleoprotein will protect animals against subsequent challenges with tumor cells that express these proteins as tumor antigens. The protection is associated with the generation of antigen specific responses among T cells in host.

Any strategy which would enhance the presentation of a particular antigen on MHC molecules of host antigen presenting cells would, in fact, enhance the immunization potential of such a viral based strategy for human cancer. The equivalent arguments can be made for generation of enhanced vaccine efficacy for viral infections such as HIV.

SUMMARY OF THE INVENTION

It is an object of this invention to provide vaccines with enhanced immunogenicity.

It is a further object of this invention to provide more effective methods of vaccination, through the use of novel immunogens which are directed to the lysosomal/endosomal compartment where they are processed and presented to major histocompatibility complex (MHC) class II molecules so that helper T cells are preferentially stimulated.

It is yet another object of this invention to provide improved methods of treatment for cancer by eliciting an anti-tumor immune response through stimulation of helper T cells.

These and other objects are achieved by the following embodiments.

In one embodiment, this invention provides a vaccine composition for eliciting an immune response in a mammal to an antigen, comprising a vaccine vector, wherein the vector contains a chimeric DNA segment which encodes a protein containing (1) an N-terminal domain containing a sequence encoding at least one epitope of said antigen, (2) a transmembrane domain and (3) a cytoplasmic domain containing an endosomal/lysosomal targeting signal directing the protein to the lysosomal membrane. In particular embodiments, the protein encoded by the chimeric DNA segment contains an intraluminal N-terminal domain comprising at least one epitope which is a peptide that complexes with major histocompatibility complex (MHC) class II molecules, and the protein has a short cytoplasmic domain which contains an endosomal/lysosomal targeting sequence near the C-terminus of the protein, the targeting sequence comprising the tetrapeptide sequence Tyr-Xaa-Xaa-Xbb, wherein Xbb is a hydrophobic amino acid.

In another embodiment, this invention provides a method of vaccination for eliciting an immune response to an antigen comprising administering to a mammal a vaccine composition containing a vector which infects the mammal, wherein the vector contains a heterologous DNA segment which encodes a protein containing (1) an N-terminal domain containing at least one epitope of said antigen, (2) a transmembrane domain and (3) a cytoplasmic domain containing an endosomal/lysosomal targeting signal directing the protein expressed from the DNA to the lysosomal membrane.

In a further embodiment, this invention provides a method of vaccination to elicit an immune response in a mammal to an antigen, comprising administering to said mammal a cell population containing an antigen presenting cell (APC) capable of replicating in said mammal, wherein the APC, after administration, will express a DNA sequence encoding (1) an N-terminal domain containing a sequence encoding at least one epitope of the antigen, (2) a transmembrane domain, and (3) a cytoplasmic domain containing an endosomal/lysosomal targeting signal directing a protein expressed from the DNA sequence to the lysosomal membrane and will also express a cell surface protein from the MHC class II group, the cell surface protein being compatible with the MHC proteins of the mammal.

In still another embodiment, this invention provides a method of treatment for a cancer patient, wherein a cell population is administered to said patient, the cell population containing an antigen presenting cell (APC) capable of replicating in said patient, wherein the APC, after administration, will express a DNA sequence encoding an N-terminal domain containing a sequence encoding at least one epitope of an antigen characteristically found on the cell surface of cells from the patient's tumor, a transmembrane domain and a cytoplasmic domain containing an endosomal/lysosomal targeting signal directing a protein expressed from the DNA sequence to the lysosomal membrane, and will also express a cell surface protein from the MHC class II group, the cell surface protein being compatible with the MHC proteins of said patient.

This invention is based on the inventors' discovery of a targeting signal that will direct proteins to the endosomal/lysosomal compartment, and their discovery that chimeric transmembrane proteins containing a luminal antigenic domain and a cytoplasmic endosomal/lysosomal targeting signal will effectively target antigens to the endosomal/lysosomal compartment in which antigen processing and association with MHC class II occurs. These findings directly support the concept of including chimeric genes involving the antigen of interest, linked to an endosomal/lysosomal targeting sequence such as that of LAMP-1, in various immunization vectors. When these vectors introduce the chimeric genes into cells, the recombinant antigens are expressed and targeted to the endosomal/lysosomal compartment where they associate more efficiently with MHC class II molecules, resulting in enhanced in vivo stimulation of $CD4^+$ T cells specific for the recombinant antigen. This represents a novel mechanism for targeting of protein antigens to the MHC class II pathway for presentation—a mechanism that will be more efficient than the earlier immunization strategies. The strategy of delivering antigens to an endosomal/lysosomal compartment by means of chimeric constructs containing such lysosomal targeting signals will be of value in any vaccination or immunization strategy that seeks to stimulate $CD4^+$ MHC class II restricted immune responses.

BRIEF DESCRIPTION OF THE DRAWINGS

FIG. 1 shows fluorescent photomicrographs of human kidney fibroblasts transfected with either unmodified or mutant LAMP-1 cDNA. After 72 hours of transient infection, the cells were fixed, permeabilized, and incubated with monoclonal antibodies specific for mouse and human LAMP-1 followed by fluorescent-conjugated secondary antibodies. FIG. 1A shows control (mock transfected) cells with anti-mouse LAMP-1 antibody. FIG. 1B shows control (mock transfected) cells with anti-human LAMP-1 antibody. FIG. 1C shows cells transfected with unmodified mouse LAMP-1 cDNA, visualized with anti-mouse LAMP-1 antibodies. FIG. 1D shows cells transfected with unmodified mouse LAMP-1 cDNA, visualized with anti-human LAMP-1 antibodies. FIG. 1E shows cells transfected with mouse LAMP-1 cDNA modified by deletion of $Ile^{382}$, visualized with anti-mouse LAMP-1 antibodies. FIG. 1F shows cells transfected with mouse LAMP-1 cDNA modified by deletion of $Ile^{382}$ and $Thr^{381}$, visualized with anti-mouse LAMP-1 antibodies. FIG. 1G shows cells transfected with mouse LAMP-1 cDNA modified by substitution of $Ile^{382}$ by Leu, visualized with anti-mouse LAMP-1 antibodies. FIG. 1H shows cells transfected with mouse LAMP-1 cDNA modified by substitution of $Ile^{382}$ by Phe, visualized with anti-mouse LAMP-1 antibodies. FIG. 1I shows cells transfected with mouse LAMP-1 cDNA modified by substitution of $Ile^{382}$ by Thr, visualized with anti-mouse LAMP-1 antibodies. FIG. 1J shows cells transfected with mouse LAMP-1 cDNA modified by substitution of $Gln^{380}$ by Ala, visualized with anti-mouse LAMP-1 antibodies. FIG. 1K shows cells transfected with mouse LAMP-1 cDNA modified by substitution of $Thr^{381}$ by Ala, visualized with anti-mouse LAMP-1 antibodies. FIG. 1L shows cells transfected with mouse LAMP-1 cDNA modified by substitution of $Gln^{380}$-$Thr^{381}$ by Ala-Ala, visualized with anti-mouse LAMP-1 antibodies.

FIG. 2 shows fluorescent photomicrographs of human kidney fibroblasts transfected with either unmodified or mutant CD44 cDNA. After 72 hours of transient infection, the cells were fixed, permeabilized, and incubated with monoclonal antibodies specific for mouse CD44 followed by fluorescent-conjugated secondary antibodies.

FIGS. 3 and 4 show graphically the results of two experiments which determined the proliferation response of anti-HA/I-$E^d$ transgenic T cells incubated with A20 antigen presenting cells transfected with modified or unmodified HA.

DETAILED DESCRIPTION OF THE INVENTION

A. Definitions

Figure 2A:
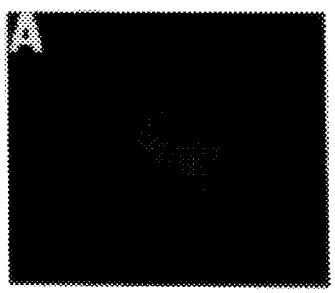
FIG. 2A shows cells transfected with unmodified mouse CD44 cDNA, visualized with anti-mouse CD44 antibodies.

The practice of the present invention employs, unless otherwise indicated, conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. I. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984).

In describing the present invention, the following terminology is used in accordance with the definitions set out below.

A "double-stranded DNA molecule" refers to the polymeric form of deoxyribonucleotides (adenine, guanine, thymine, or cytosine) in its normal, double-stranded helix. In discussing the structure of particular double-stranded DNA molecules, sequences may be described herein according to the normal convention of giving only the sequence in the 5' to 3' direction along the nontranscribed stand of DNA (i.e., the strand having a sequence homologous to the mRNA).

A "chimeric DNA" is an identifiable segment of DNA within a larger DNA molecule that is not found in association with the larger molecule in nature. Thus, when the chimeric DNA encodes a protein segment, the segment coding sequence will be flanked by DNA that does not flank the coding sequence in any naturally occurring genome. Allelic variations or naturally occurring mutational events do not give rise to a chimeric DNA as defined herein.

A coding sequence is an in-frame sequence of codons that (in view of the genetic code) correspond to or encode a protein or peptide sequence. Two coding sequences correspond to each other if the sequences or their complementary sequences encode the same amino acid sequences. A "coding sequence" in association with appropriate regulatory sequences may be transcribed and translated into a polypeptide in vivo. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. A coding sequence is "under the control" of the promoter sequence in a cell when RNA polymerase which binds the promoter sequence transcribes the coding sequence into mRNA which is then in turn translated into the protein encoded by the coding sequence.

A cell has been "transformed" by exogenous DNA when such exogenous DNA has been introduced inside the cell wall. Exogenous DNA may or may not be integrated (covalently linked) to chromosomal DNA making up the genome of the cell. In procaryotes and yeast, for example, the exogenous DNA may be maintained on an episomal element such as a plasmid. With respect to eukaryotic cells, a stably transformed cell is one in which the exogenous DNA has become integrated into a chromosome so that it is inherited by daughter cells through chromosome replication. This stability is demonstrated by the ability of the eukaryotic cell to establish cell lines or clones comprised of a population of daughter cells containing the exogenous DNA. A "clone" is a population of cells derived from a single cell or common ancestor by cell division. A "cell line" is a clone of a primary cell that is capable of stable growth in vitro for many generations.

A "replicon" is any genetic element (e.g., plasmid, chromosome, virus) that functions as an autonomous unit of DNA replication in vivo.

A "vector" is an agent used to introduce a foreign substance, such as DNA, RNA or protein, into an organism. Typical vectors include recombinant viruses (for DNA) and liposomes (for protein).

An "epitope" is a structure, usually made up of a short peptide sequence or oligosaccharide, that is specifically recognized or specifically bound by a component of the immune system. T-cell epitopes have generally been shown to be linear oligopeptides. Two epitopes correspond to each other if they can be specifically bound by the same antibody. Two antibodies correspond to each other if both are capable of binding to the same epitope, and binding of one antibody to its epitope prevents binding by the other antibody.

B. The Targeting Sequence of Lysosomal Membrane Glycoproteins:

The known cytoplasmic tail sequences of lysosomal membrane proteins, LAMP-1 (Chen, et al., 1988), LAMP-2 (Cha, et al., 1990) and CD63 (Hotta, et al., *Cancer Res.*, 48:2955, 1988), have been aligned by the inventors with the Tyr-containing internalization signal in the cytoplasmic tail of LAP (Pohlman, et al., 1988) in Table 1. The Tyr is known to be required for endosomal/lysosomal targeting, and it is demonstrated herein that the complete sequence required to target other molecules to lysosomes requires the Tyr-X-X-hyd sequence, a Tyr followed by two amino acids followed by a hydrophobic residue.

TABLE 1

Cytoplasmic tail sequences of the major lysosomal membrane proteins.

The conserved Gly-Tyr-X-X-hydrophobic residue motif in the cytoplasmic domain of the described lysosomal membrane proteins is underlined, where X is any amino acid. The complete cytoplasmic tail sequence of the listed proteins is shown from the transmembrane region to the carboxyl terminus.

| LAMP-1: | R K R S H A G Y O T I |
| LAMP-2: | K H H A G Y E O F |
| CD63: | K S I R S G Y E V M |
| LAP: | R M E A P P G Y R H V A D G Q D H A |

The importance of a hydrophobic residue at or near the carboxyl-terminal position is shown by the results obtained from modification of the Tyr-Gln-Thr-Ile sequence of LAMP-1. Mutant cDNA molecules were constructed in which Ile was substituted with two other hydrophobic residues, Leu or Phe, and a polar residue, Thr. Substituting Leu (Tyr-Gln-Thr-Leu) and Phe (Tyr-Gln-Thr-Phe) did not affect lysosomal targeting, whereas the Thr-containing mutant protein (Tyr-Gln-Thr-Thr) accumulated at the cell surface. The role of Gln and Thr was analyzed using three additional mutants containing Ala substituted for Gln (Tyr-Ala-Thr-Ile), Thr (Tyr-Gln-Ala-Ile), and both residues (Tyr-Ala-Ala-Ile). These substitutions had no effect on targeting of the protein to the lysosomal membrane, indicating that these positions may be occupied by charged, polar, or nonpolar residues.

Additional constructs indicate that the Tyr-Gln-Thr-Ile sequence, while sufficient to confer lysosomal membrane targeting, must occur in a specific context to mediate lysosomal signaling. Non-truncated mutant proteins having the sequence Tyr-Gln-Thr-Ile inserted in the middle of a long (~70 amino acid) cytoplasmic sequence or having the motif placed at the end of a long cytoplasmic sequence were not targeted to lysosomes, but rather appeared on the plasma membrane.

C. The Modification of Other Proteins for the Purpose of Targeting These Proteins to Endosomal/Lysosomal Compartment The present invention provides immune stimulatory constructs composed of (1) an antigenic polypeptide domain containing one or more peptide segments which, when released by proteolytic enzymes, will complex with MHC class II molecules; (2) a transmembrane domain, and (3) a cytoplasmic tail containing an endosomal/lysosomal targeting signal that targets the antigenic domain to the compartment capable of antigen processing and presentation to MHC class II molecules. It further provides heterologous or chimeric DNA encoding such constructs which also contain appropriate control sequences followed in order by: a translation initiation site in reading frame with a signal sequence that will direct expression to the secretory compartment, the antigenic domain, a hydrophobic transmembrane domain, the cytoplasmic tail containing the endosomal/lysosomal targeting signal and a translational stop signal. Replicons containing this heterologous DNA are also provided by this invention.

Usually the replicons are capable of expressing the immune stimulatory construct in vivo in a mammalian cell. Expression of the heterologous DNA of this invention by an antigen presenting cell will result in targeting of the immune stimulatory construct to the lysosomal/endosomal compartment, where peptide segments will be released to complex with MHC class II molecules, resulting in stimulation of the CD4⁺ T cell population specific for the antigenic domain of the construct.

1. Antigenic Domain

As regards the antigenic material, the present invention is widely applicable to antigenic materials which are of use in vaccines or in other contexts. The term "antigenic material" as used herein covers any substance that will elicit a specific immune response when processed and presented in combination with an MHC class II molecule. This antigenic material will generally contain peptide segments that can be released by lysosomal enzymes and, when released, correspond to MHC class II epitopes. The antigenic material may also contain regions which stimulate other components of the immune system.

Because the constructs of the present invention traverse the post-translational modification compartments prior to transport to the lysosomal compartment, the antigenic domain may also include epitopes resulting from cellular modification. Essentially, any polypeptide that can be synthesized by a mammalian cell and contains epitopes which can be complexed by MHC II molecules may be incorporated into the antigenic domain, either directly in primary amino acid sequence or in signals directing its creation during post-translational processing. Selection of the most appropriate portion of the desired antigen protein for use as the antigenic domain can be done by functional screening. Broadly, this screening method involves cloning DNA encoding one or more segments of the protein antigen as the antigenic domain of DNA encoding an immune stimulatory construct as taught herein; preferably, such a construct will incorporate the transmembrane domain and cytoplasmic tail of LAMP-1. The cloned DNA is expressed, preferably in an antigen presenting cell line.

The particular screening procedure depends upon the type of antigen and the assays for its antigenic activity. Antigenicity may be measured by stimulation of antigen-specific MHC class II specific T cell line or clone. Alternatively, antigenicity may be determined by measurement of the ability to generate antibodies or T cells specific for the antigen in vivo. These and other tests of antigenic activity are well known to those skilled in the art.

Antigens that may serve as the source of preferred antigenic material include tumor antigens, auto-antigens, cell surface proteins found on mammalian cells, proteins of bacteria, protozoa or fungi, including especially proteins found in the cell walls or cell membranes of these organisms, and proteins encoded by the genomes of viruses including retroviruses such as HIV and hepadnaviruses. Particularly preferred antigens are antigens encoded by the genomes of organisms causative for or associated with hepatitis, rabies, malaria, schistosomiasis, cancer, AIDS, yellow fever, dengue fever, equine encephalitis, Rift valley fever, cat scratch fever, viral meningitis. Particularly preferred viral antigens are virally-encoded proteins encoded by the genome of viruses pathogenic to man, horses, cows, pigs, llamas, giraffes, dogs, cats or chickens.

2. Transmembrane Domain

The structure of a transmembrane domain in a polypeptide is well known in the art (see, e.g., Bangham, *Anal. Biochem.*, 174:142, 1988; Klein, et al., *Biochem. Biophys. Acta*, 815:468, 1985; Kyle & Doolittle, *J. Mol. Biol.*, 157:105, 1982). Usually the transmembrane region appears in the primary sequence as a sequence of 20–25 hydrophobic amino acid residues flanked by more hydrophilic regions. Such sequences can be found, for example, in most cell surface antigen sequences listed by Genebank as well as many other membrane proteins. The particular transmembrane sequence is not critical, so long as it serves to connect the antigenic domain to the cytoplasmic tail and anchor the construct in the membranous compartment.

Many proteins that will serve as the source of the antigenic domain for particular immune stimulatory constructs will be surface antigens that include a transmembrane domain in their primary sequence. Such a transmembrane domain can be retained, and the cytoplasmic domain replaced with a lysosomal/endosomal targeting signal as taught herein. Alternatively, the transmembrane domain of LAMP, preferably with the LAMP cytoplasmic tail attached (see Chen, et al., *J. Biol. Chem.*, 263:8754, 1988, incorporated herein by reference), can be connected to the primary sequence of the desired antigenic domain to direct the construct to lysosomal processing for presentation via the MHC II/helper T cell system.

3. Lysosomal/Endosomal Targeting Signal

Any sequences may be used which contain a signal that confers endosomal/lysosomal targeting. Examples of such sequences occur in the cytoplasmic domains of various lysosomal/endosomal membrane glycoproteins and receptors which cycle between endosomes and the plasma membrane. Sequences containing the targeting signal may be identified by constructing a chimeric DNA containing the antigenic domain of HA, a transmembrane domain, and the cytoplasmic domain of a protein containing a putative lysosomal/endosomal targeting signal. Efficiency of targeting is measured by the ability of antigen presenting cells, expressing the chimeric protein, to stimulate HA epitope specific, MHC class II restricted T-cells (see, e.g., Example 5 below).

The preferred targeting signal to the lysosomal/endosomal compartment includes a tetrapeptide sequence located in the cytoplasmic domain, near the transmembrane domain and also near the C-terminus. The cytoplasmic domain is preferably a short amino acid sequence (less than 70 amino acids, preferably less than 30 amino acids, most preferably less than 20 amino acids) ending in a free carboxyl group. In a more preferred embodiment, the tetrapeptide is at the C-terminal end of a short cytoplasmic tail that contains the targeting signal, or is in a context similar to LAMP-1. A suitable four amino acid sequence for the tetrapeptide may be obtained by amino acid substitutions, so long as the motif consists of Tyr-X-X-Hyd (where X may be any amino acid and Hyd denotes a hydrophobic amino acid), and the ability to confer lysosomal/endosomal targeting is conserved. A particularly preferred tetrapeptide has the sequence Tyr-Gln-Thr-Ile. In the most preferred embodiment, the entire LAMP cytoplasmic tail in conjunction with its transmembrane domain may be connected to the primary sequence of the antigenic domain for highly efficient MHC class II processing and presentation.

4. Assembly of Sequences Encoding the Immunogen

Procedures for construction of chimeric proteins are well known in the art (see e.g., Williams, et al., *J. Cell Biol.*, 111:955, 1990, incorporated by reference). Broadly, DNA sequences encoding the desired segments are obtained from readily available recombinant DNA materials such as those available from the American Type Culture Collection, 12301 Parklawn Drive, Rockville, Md. 20852, U.S.A., or from DNA libraries that contain the desired DNA. The DNA segments corresponding to the antigenic domain, the transmembrane domain and the lysosomal targeting sequence (cytoplasmic tail) are then assembled with appropriate control and signal sequences using routine procedures of recombinant DNA methodology. The procedure is generally similar to that taught in U.S. Pat. No. 4,593,002, and in Langford, et al., *Molec. Cell. Biol.*, 6:3191, 1986 (all of which are incorporated herein by reference), except for the addition of lysosomal targeting sequences to the constructs of this invention.

A DNA sequence encoding a protein or polypeptide can be synthesized chemically or isolated by one of several approaches. The DNA sequence to be synthesized can be designed with the appropriate codons for the desired amino acid sequence. In general, one will select preferred codons for the intended host in which the sequence will be used for expression. The complete sequence may be assembled from overlapping oligonucleotides prepared by standard methods and assembled into a complete coding sequence. See, e.g., Edge (1981) *Nature* 292:756; Nambair, et al. (1984) *Science* 223:1299; Jay, et al. (1984) *J. Biol. Chem.*, 259:6311.

Preferably, the antigenic domain, transmembrane domain, and lysosomal/endosomal targeting signal-containing cytoplasmic domain may be isolated individually using the polymerase chain reaction (M. A. Innis, et al., "PCR Protocols: A Guide To Methods and Applications," Academic Press, 1990). The domains are preferably isolated from publicly available clones known to contain them, but they may also be isolated from genomic DNA or cDNA libraries. The conditions of the reaction are such that the isolated fragments are bordered by compatible restriction endonuclease sites which allow a chimeric DNA, encoding the immunogenic protein sequence, to be constructed. This technique is well known to those of skill in the art.

The basic strategies for preparing oligonucleotide primers, probes and DNA libraries, as well as their screening by nucleic acid hybridization, are well known to those of ordinary skill in the art. See, e.g., Sambrook, et al., "Molecular Cloning: a Laboratory Manual" (1989); B. Perbal, "A Practical Guide To Molecular Cloning" (1984). The construction of an appropriate genomic DNA or cDNA library is within the skill of the art. See, e.g., B. Perbal, supra. Alternatively, suitable DNA libraries or publicly available clones are available from suppliers of biological research materials, such as Clonetech and Stratagene, as well as public depositories such as the American Type Culture Collection.

Selection may be accomplished by expressing sequences from an expression library of DNA and detecting the expressed peptides immunologically. Clones which express peptides that bind to MHC II molecules and to the desired antibodies/T cell receptors are selected. These selection procedures are well known to those of ordinary skill in the art (see, e.g., Sambrook, et al.).

Once a clone containing the coding sequence for the desired polypeptide sequence has been prepared or isolated, the sequence can be cloned into any suitable replicon and thereby maintained in a composition which is substantially free of replicons that do not contain the coding sequence. Numerous replicons for cloning are known to those of skill in the art, and the selection of an appropriate replicon is a matter of choice (see, e.g., Sambrook, et al., incorporated herein by reference). The DNA sequences and DNA molecules of the present invention may be expressed using a wide variety of host/replicon combinations. In a preferred embodiment of the present invention, the coding sequence for the polypeptide is placed under the control of a promoter, ribosome binding site (for expression) and, optionally, an operator (collectively referred to herein as "control" elements), so that the DNA sequence is transcribed into RNA in the host cell transformed by a replicon containing this expression construct. The coding sequence preferably contains a signal peptide or leader sequence.

Preferably, the replicons of this invention will be infectious for cells of animals, including man, horses, cows, pigs, llamas, giraffes, dogs, cats or chickens, and more preferably the replicons will infect these organisms. Particularly preferred replicons include the vaccine vectors described below.

D. Recombinant Vaccines

This invention has general application to all recombinant vaccines, regardless of the vector or antigen, provided the vector enters cells that contain MHC class II molecules and that present antigen to T cells. Examples of such cell types include cells of dendritic, macrophage, mastocytoma and B cell lineages, whether the cells be stem cells of other antigen presenting cell precursors, cells that can be induced to become antigen presenting cells, or mature antigen presenting cells.

The method of this invention is contemplated for all immunization or vaccination strategies that contemplate MHC class II-restricted T cell responses. Diseases for which this therapy is particularly applicable include all infectious diseases, cancer, and autoimmune diseases.

Major efforts in current vaccine research are directed to expression of antigenic proteins by microbial vectors. Recombinant expression vectors may be derived from micro-organisms which readily infect animals, including man, horses, cows, pigs, llamas, giraffes, dogs, cats or chickens. Preferred vectors include those which have already been used as live vaccines, such as vaccinia. These recombinants can be directly inoculated into a host, conferring immunity not only to the microbial vector, but also to expressed foreign antigens. Preferred vectors contemplated herein as live recombinant vaccines include RNA viruses, adenovirus, herpesviruses, poliovirus, and vaccinia and other pox viruses, as taught in Flexner, *Adv. Pharmacol.*, 21:51, 1990, incorporated herein by reference.

1. Recombinant Viruses

Most viruses can be engineered for expression of foreign proteins or epitopes. As early as 1978, foreign DNA sequences were introduced into large DNA viruses through homologous recombination and marker rescue (reviewed by Roizman and Jenkins, *Science*, 229:1208, 1985). Shortly thereafter, such recombinants were proposed as live vaccines. Although the technique was developed for herpes simplex virus, homologous recombination is useful for insertion of foreign DNA into other large DNA viruses, such as poxviruses (Moss and Flexner, *Ann. Rev. Immunol.*, 5:305, 1987).

RNA viruses such as poliovirus have been used to express heterologous epitopes, but small RNA viruses are tightly packaged, contain few nonessential regions of DNA, and thus have limited capacity for foreign polypeptide expression. Smaller DNA viruses and RNA viruses may then be limited to expression of a single antigenic protein, or small polypeptides. Other virus vectors are widely used for protein expression, but their inability to replicate in mammalian hosts (e.g., baculovirus) or problems with constitutive protein expression and oncogenicity (e.g., retroviral vectors) may limit their use in vaccines.

The use of vaccinia as a live virus vaccine in the global campaign to eradicate smallpox made vaccinia an obvious choice for development as a live recombinant vaccine vector. Live recombinant vaccinia viruses expressing close to 100 different foreign proteins have been reported, and a number of these are effective experimental vaccines (reviewed by Moss and Flexner, 1987). Vaccinia is particularly versatile as an expression vector because of its large genomic size, capability of accepting at least 25,000 base pairs of foreign DNA, and its ability to infect most eukaryotic cell types, including insect cells (ibid.). Unlike other DNA viruses, poxviruses replicate exclusively in the cytoplasm of infected cells, reducing the possibility of genetic exchange of recombinant viral DNA with the host chromosome. Recombinant vaccinia vectors have been shown to properly process and express proteins from a variety of sources including man, other mammals, parasites, RNA and DNA viruses, bacteria and bacteriophage. The virus is capable of infecting most mammals, making it a useful vector for studying a broad range of human and animal diseases.

Construction of live recombinant microorganisms is based on standard techniques familiar to those skilled in the art. (The following description covers procedures that may be used with vaccinia virus, but similar procedures that may be used with other vectors are known to those skilled in the art.) The expression of DNA encoding a foreign protein is controlled by host virus regulatory elements, including upstream promoter sequences and, where necessary, RNA processing signals. Insertion of foreign DNA into nonessential regions of the vaccinia virus genome has been carried out by homologous recombination (Panicali, et al., *Proc. Nat'l. Acad. Sci, USA*, 79:4927, 1982; Mackett, et al., *Proc. Nat'l. Acad. Sci. USA*, 79:7415, 1982). Expression of foreign genes within the DNA may occur because of transcriptional regulatory elements at or near the site of insertion or by more precise genetic engineering. Plasmid vectors that greatly facilitate insertion and expression of foreign genes have been constructed (Mackett, et al., *J. Virol.*, 49:857, 1982). These vectors contain an expression site, composed of a vaccinia transcriptional promoter and one or more unique restriction endonuclease sites for insertion of the foreign coding sequence flanked by DNA from a nonessential region of the vaccinia genome. The choice of promoter determines both the time (e.g. early or late) and level of expression, whereas the flanking DNA sequence determines the site of homologous recombination.

Only about one in a thousand virus particles produced by this procedure is a recombinant. Although recombinant virus plaques can be identified by DNA hybridization, efficient selection procedures have been developed. By using segments of nonessential vaccinia virus thymidine kinase (TK) gene as flanking sequences, the foreign gene recombines into the TK locus and by insertion inactivates the TK gene. Selection of TK virus is achieved by carrying out the virus plaque assay in TK cells in the presents of 5-bromodeoxyuridine. Phosphorylation of the nucleoside analogue and consequent lethal incorporation into viral DNA occurs only in cells infected with TK$^+$ parental virus. Depending on the efficiency of the transfection and recombination, up to 80 of the plaques are desired recombinants, and the rest are spontaneous TK mutants.

Plasmid vectors that contain the *E. coli* β-galactosidase gene, as well as an expression site for a second gene, permit an alternative method of distinguishing recombinant from parental virus (Chakrabarti, et al., *Mol. Cell. Biol.*, 5:3403, 1985). Plaques formed by such recombinants can be positively identified by the blue color that forms upon addition of an appropriate indicator. By combining both TK selection and β-galactosidase expression, recombinant virus is readily and quickly isolated. The recombinants are then amplified by propagation in suitable cell lines and expression of the inserted gene is checked by appropriate enzymological, immunological or physical procedures.

An upper limit to the amount of genetic information that can be added to the vaccinia virus genome is not yet known. However, the addition of nearly 25,000 base pairs of foreign DNA had no apparent deleterious effect on virus yield (Smith, et al., *Gene*, 25:21, 1983). Were it necessary, large segments of the vaccinia virus genome could be deleted to provide additional capacity (Moss, et al., *J. Virol.*, 40:387, 1981).

2. Peptide Vaccines

Also within the contemplation of this invention are vaccines containing cell-free peptide immunogens, where the immunogen contains the transmembrane region and cytoplasmic tail with lysosomal targeting region, corresponding to immune stimulatory constructs encoded by the DNA sequences described above. The immune stimulatory construct may be bound in a membranous structure for administration as a vaccine. Such immunogens are preferably incorporated into liposomes, for instance as described in U.S. Pat. No. 4,448,765, incorporated herein by reference.

When a protein or polypeptide is to be used as an immunogen, it may be produced by expression of the DNA in a recombinant cell or it may be prepared by chemical synthesis. For example, the Merrifield technique (*Journal of American Chemical Society*, vol. 85, pp. 2149–2154, 1968), can be used.

3. Administration

Vaccine material according to this invention may contain the immune stimulatory constructs described above or may be recombinant micro-organisms which express the immune stimulatory constructs. Preparation of compositions containing vaccine material according to this invention and administration of such compositions for immunization of individuals are accomplished according to principles of immunization that are well known to those skilled in the art. Large quantities of these materials may be obtained by culturing recombinant or transformed cells containing replicons that express the chimeric DNA described above. Culturing methods are well-known to those skilled in the art and are taught in one or more of the documents cited above. The vaccine material is generally produced by culture of recombinant or transformed cells and formulated in a pharmacologically acceptable solution or suspension, which is usually a physiologically-compatible aqueous solution, or in coated tablets, tablets, capsules, suppositories or ampules, as described in the art, for example in U.S. Pat. No. 4,446,128, incorporated herein by reference. Administration may be any suitable route, including oral, rectal, intranasal or by injection where injection may be, for example, transdermal, subcutaneous, intramuscular or intravenous.

The vaccine composition is administered to a mammal in an amount sufficient to induce an immune response in the mammal. A minimum preferred amount for administration is the amount required to elicit antibody formation to a concentration at least 4 times that which existed prior to administration. A typical initial dose for administration would be 10–100 micrograms when administered intravenously, intramuscularly or subcutaneously, 100 to 1000 micrograms by mouth, of the immune stimulatory construct, or $10^5$ to $10^{10}$ plaque forming units of a recombinant vector, although this amount may be adjusted by a clinician doing the administration as commonly occurs in the administration of vaccines and other agents which induce immune responses. A single administration may usually be sufficient to induce immunity, but multiple administrations may be carried out to assure or boost the response.

Further description of suitable methods of formulation and administration according to this invention may be found in the following U.S. patents, incorporated herein by reference: U.S. Pat. No. 4,454,116 (constructs), U.S. Pat. No. 4,681,762 (recombinant bacteria), and U.S. Pat. Nos. 4,592,002 and 4,920,209 (recombinant viruses).

E. Transfected Antigen Presenting Cells

A strategy to utilize enhanced antigen presentation for immunization is to remove antigen presenting cells from the body, culture the cells in vitro, and transfect these cells with an appropriate vector encoding the antigen of interest modified with the LAMP targeting signal, as described above. These transduced antigen presenting cells now express the antigen of interest and can be re-injected into the individual, thereby generating immune responses. An example of this strategy would be the infection or transformation of CD34+ precursors that are differentiating under the influence of GM-CSF into dendritic cells followed by re-injection of these transduced dendritic cells. Utilizing the construct containing antigenic sequences linked to an endosomal/lysosomal targeting signal will enhance the association of peptides derived from a particular antigen with MHC class II molecules on the transduced antigen presenting cells, resulting in significantly more potent systemic T cell dependent immune responses. While the antigen presenting cells transfected in this strategy are preferably autologous cells, any MHC class II$^+$ cells that effectively present antigen in the host may be used.

F. Immune Tolerance and Autoimmunity

Many auto-immune diseases show a correlation with certain MHC class II haplotypes and are associated with aberrant auto-antibody production, suggesting that the generation of self-reactive MHC class II restricted CD4$^+$ T cells is an important pathogenetic step. Given that CD4$^+$ cells can, under certain circumstances, be inactivated or anergized by engagement of their T cell receptor in the absence of a second signal (such as the co-engagement of CD28 by its ligand B7), it follows that the efficient presentation of an MHC class II restricted antigen on an MHC class II$^+$ cell that did not display the appropriate second signal would represent an effective toleragen. The generation of this tolerance or inactivation of certain CD4$^+$ T cells could be used to turn off aberrant immune responses in auto-immune diseases.

In the embodiment of this principle, a poor antigen presenting cell (that did not express any co-stimulatory signals) would either be induced to express MHC class II or would be transfected with the appropriate MHC class II genes. This cell would then be additionally transduced with the auto-antigen of interest, such as the acetylcholine receptor in the case of myaesthenia gravis, linked to the endosomal/lysosomal targeting signal. Injection of these cells into the host would result in turning off T cell responses against the antigen, based on the efficient presentation of peptide sequences on MHC class II molecules to T cell receptors on CD4$^+$ T cells in the absence of the appropriate co-stimulatory signals (signals that are provided by effective antigen present cells).

G. Cancer Immunotherapy

1. Candidates for Treatment

Candidates for cancer immunotherapy would be any patient with a cancer possessing a defined and identified tumor specific antigen whose gene can be cloned and modified by the LAMP lysosomal/endosomal targeting sequences as described herein. Examples include patients with documented Epstein-Barr virus associated lymphomas, patients with HPV associated cervical carcinomas, or patients with a defined re-arrangement or mutation in an oncogene or tumor suppressor gene. It is envisioned that therapy with a vaccine incorporating the tumor antigen linked to the lysosomal/endosomal targeting sequences in a viral vaccine could be utilized at any period during the course of the individual's cancer, once it is identified. It is also possible that in high risk patients, vaccination in order to prevent the subsequent emergence of a cancer with a defined tumor specific antigen could be performed.

2. Procedure for Therapy

In one embodiment, recombinant viral vaccine containing the antigen linked with the lysosomal/endosomal targeting sequence incorporated into a viral vaccine such as vaccinia, would be produced in large quantities as described above and would be injected into the patient at any suitable time during the course of their malignancy. Preferably, the vaccine would be injected at a stage when the tumor burden was low. In an alternative embodiment in which this construct is introduced into the individual's antigen presenting cells, precursors to the antigen presenting cells or mature antigen presenting cells are drawn either from the individual's bone marrow or peripheral blood by vena puncture. These cells are established in culture followed by transduction with the chimeric construct. Once transduction had occurred, these antigen presenting cells are injected back into the patient.

In a particularly preferred embodiment, the invention provides a method of treatment for a cancer patient having low tumor burden, such as early in the disease, after resection of a neoplastic tumor, or when the burden of tumor cells is otherwise reduced. In this method, once a tumor-specific cell surface antigen characteristic of the patient's tumor has been identified, a cell population containing autologous stem cells capable of differentiation into antigen presenting cells which will express MHC class II molecules is obtained from the patient. These cells are cultured and transformed by introducing a heterologous or chimeric DNA molecule which encodes a protein containing (1) an N-terminal domain containing at least one epitope of the tumor-specific antigen found on the cells of the patient's tumor, (2) a transmembrane domain and (3) a cytoplasmic domain containing an endosomal/lysosomal targeting signal directing the protein to the lysosomal membrane, i.e., the DNA encodes the immune stimulatory construct described above. The transfected stem cell population is then reintroduced into the patient, where the stem cells differentiate into antigen presenting cells which express MHC class II molecules complexed with $T_h$ epitopes from the tumor-specific antigen. The immune response to the tumor-specific antigen will be enhanced by enhanced stimulation of the helper T cell population.

The following Examples are provided for purposes of illustration only. They are not intended to limit the invention described above, which is only limited by the appended claims.

EXAMPLES

Example 1

Analysis of Mutant LAMP-1 Proteins Containing Serial Deletions at the Cytoplasmic Tail We constructed a series of mutant LAMP-1 cDNA molecules containing step-wise deletions in the cytoplasmic tail: deletion Ile$^{382}$; deletion Ile$^{382}$ and Thr$^{381}$; deletion Ile$^{382}$, Thr$^{381}$ and Gln$^{380}$; and deletion Ile$^{382}$, Thr$^{381}$, Gln$^{380}$ and Tyr$^{379}$.

Site-directed Mutagenesis and Subcloning of Mutated LAMP-1 cDNA

Deletion mutants were prepared using the polymerase chain reaction. The template was the linear LAMP-1 cDNA clone 9E5 (Cha, et al., 1990). The sense primer annealed to the sequence corresponding to amino acid residues $Ser^{102}$ to $Asp^{108}$, 54 base pairs 5'- of an EcoR V restriction site. The following antisense primers were used to generate deletions (premature stop codon is in bold, Xho I restriction site is bound with brackets):

Deletion $Tyr^{379}$, $Gln^{380}$, $Thr^{381}$, and $I^{382}$: 5'-ctctaga[ctcgagg]ctagccggcgtgactcctct-3'
Deletion $Gln^{380}$, $Thr^{381}$, and $Ile^{382}$: 5'-ctctaga[ctcgagg]ctaatagccggcgtgactcc-3'
Deletion $Thr^{381}$ and $Ile^{382}$: 5'-ctctaga[ctcgagg]ctactgatagccggcgtga-3'
Deletion $Ile^{382}$: 5'-ctctaga[ctcgagg]ctaggtctgatagccggcgt-3'

The approximately 850 base pair PCR products were isolated on a 2% agarose gel and purified using GENE CLEAN (Bio-101). A plasmid containing the LAMP-1 clone 9E5 inserted into the EcoR I restriction site of the vector PcDNA I (Invitrogen) was cut with EcoRV and Xho I. The wild type insert resulting from this cut was removed and replaced with the deletion encoding inserts.

The murine cDNA molecules were transfected and transiently expressed for 72 hrs in human embryonic kidney fibroblasts. The cells were fixed and permeabilized, and monoclonal antibodies with appropriate fluorescent-conjugated second antibodies were used to distinguish, and where applicable colocalize the transfected murine and endogenous human LAMP-1, the control for lysosomal localization, in the same cell.

Transfections and Immunofluorescence: 1.5 ml ($10^5$ cells per ml) 293S human embryonic kidney cells growing in 90% DMEM/F12 (Gibco), 10% fetal calf serum (Gibco), were placed in a sterile 35 mm tissue culture dish containing a sterile coverslip. Cells were incubated overnight at 37° C. with $CO_2$. Media was changed 3 hours prior to transfections. Immediately prior to transfections, 10 ul of 2.5M $CaCl_2$ was added to 90 ul of 1 mM tris HCl (pH 7.5), 0.1 mM EDTA containing 5 ug of LAMP-1 (normal or mutated) plasmid DNA. To this solution was added 100 ul 2× Hepes buffered saline. The DNA slurry was added to the dishes. After 4 hrs at 37° C., media was aspirated from the dishes and 1 ml 15% glycerol in phosphate buffered saline (PBS) was added. After 30 seconds, cells were washed with PBS and 1.5 ml of media was added. At 72 hrs, cells were fixed in 4% paraformaldehyde in PBS. Cells were then incubated for 15 min with 0.1% saponin and 4% normal goat serum in PBS. Cells transfected with LAMP-1 were then incubated with 0.7 ml of an equal mixture of ID4B (rat anti-mouse LAMP-1 monoclonal antibody, Chen, et al., 1985) and H5G11 (mouse anti-human LAMP-1 monoclonal antibody, Mane, et al., Arch. Biochem. Biophys., 268:360, 1989), and 0.1% saponin for 30 min. After washing with PBS containing 0.1% saponin, cells were incubated for 30 min with PBS containing 10 ug/ml Texas Red-conjugated goat anti-rat IgG, 20 ug/ml FITC-conjugated goat anti-mouse IgG (Jackson Immunochemicals), and 0.1% saponin. Cells were washed 3 times with PBS and the coverslip was inverted onto a slide containing a drop of 25% glycerol in PBS. The slides were observed using a Zeiss Axiophot under a 63× oil immersion lens. Exposures were manually adjusted to one quarter the automatic setting using 400 TMAX film (Kodak).

All deletion mutants, including those that contained the critical Tyr, accumulated at the cell surface instead of at the lysosomal membrane (deletion $Ile^{382}$, FIG. 1E; deletion $Ile^{382}$ and $Thr^{381}$, FIG. 1F; the two additional mutants with larger deletions are not shown). In contrast, unmodified murine LAMP-1 was targeted to the lysosomal membrane (FIG. 1C) as indicated by colocalization with human LAMP-1 (FIG. 1D). No nonspecific staining was observed in the untransfected human cells (FIGS. 1A and B). These data indicate that the carboxyl-terminal $Ile^{382}$, and possibly $Thr^{381}$ and $Gln^{380}$ also, plays an important role in the targeting of LAMP-1.

Example 2

Analysis of Mutant LAMP-1 Proteins With Amino Acid Substitutions at the Terminal Three Positions (380–382) of the Cytoplasmic Tail The above data together with the known cytoplasmic tail sequences of two additional lysosomal membrane proteins, LAMP-2 (Cha, et al., 1990) and CD63 (Metzelaar, et al., J. Biol. Chem., 266:3239, 1991), and the presence of a Tyr-containing internalization signal in the cytoplasmic tail of LAP (Peters, et al., 1990), suggest that the lysosomal targeting signal for these molecules is a consensus sequence composed of a Tyr followed by two amino acids, at least one of which is polar or charged, followed by a hydrophobic residue (Table I). The importance of a hydrophobic residue at the carboxyl-terminal position was supported by the results obtained with three mutant cDNA molecules in which $Ile^{382}$ was substituted with two other hydrophobic residues, Leu or Phe, and a polar residue, Thr.

Substitution and insertion mutations were prepared using the Amersham Site directed Mutagenesis Kit. Antisense strand of LAMP-1 clones was subcloned into the EcoRI site of M13mp18. The following primers were used for LAMP-1 mutations (primers are sense, mismatches are in bold):

Substitution Ile382 to Leu: 5'-ggetatcagaccctctag-3'
Ile382 to Phe: 5'-ggctatcagaccttctag-3'
$Ile^{382}$ to Thr: 5'-gctatcagaccacctagc-3'
$Gln^{380}$ to Ala: 5'-cgccggctatgcgaccatctag-3'
$Thr^{381}$ to Ala: 5'-cggctatcaggccatetagcc-3'
$Gln^{380}$-$Thr^{381}$ to Ala-Ala: 5'-cacgecggctatgcggccatctagcctg-3'

Substituting Leu (Tyr-Gln-Thr-Leu) and Phe (Tyr-Gln-Thr-Phe) did not affect lysosomal targeting, whereas the Thr (Tyr-Gln-Thr-Thr) containing mutant protein accumulated at the cell surface (FIGS. 1G–I). The role of positions 380 and 381 was analyzed using three additional mutants containing Ala substituted for $Glu^{380}$ (Tyr-Ala-Thr-Ile), $Thr^{381}$ (Tyr-Gln-Ala-Ile), and both residues (Tyr-Ala-Ala-Ile). These substitutions had no effect on targeting of the protein to the lysosomal membrane, indicating that these positions may be occupied by charged, polar, or nonpolar residues (FIGS. 1J–L).

Example 3

Substitution of the Amino Acids Tyr-Gln-Thr-Ile into the Cytoplasmic Tail of a Resident Plasma Membrane Protein Additional experiments were performed to determine if the sequence Tyr-Gln-Thr-Ile was sufficient for protein targeting to the lysosomal membrane. For this purpose, these amino acids were inserted into the cytoplasmic tail of murine CD44 (Hughes, et al., J. Biol. Chem., 265:664, 1981), a type I cell membrane glycoprotein and hyaluronate receptor not associated with the lysosomal membrane. This glycoprotein consists of 345 amino acids with an extracellular domain of 252 amino acids, a single 21-residue transmembrane-spanning domain, and a cytoplasmic domain of 72 amino acids.

A modified murine CD44 cDNA, encoding a protein in which 65 carboxyl-terminal residues were deleted and replaced with the sequence Tyr-Gln-Thr-Ile-End (placed after $Gly^{280}$), was constructed. In this construct, the four-amino-acid signal was located at the end of an eleven-amino acid cytoplasmic tail, the same context as in LAMP.

Substitution and insertion mutations were prepared using the Amersham Site directed Mutagenesis Kit. Sense strand of murine CD44 (Wolffe, et al., *J. Biol. Chem.*, 265:341, 1990) clones was subcloned into the Hind III - XbaI site of M13mp19. The following primers were used for insertion mutations in CD44 (primers are anti-sense; CD44 amino acid positions interrupted by insertion are numbered in superscript; inserted sequences are bound by brackets):

Insertion $Gly^{280}$-[Tyr-Gln-Thr-Ile]-$Gly^{281}$: 5'-ccagcttttcttetg[gatggtctgata]cccacaccttctcct-3'
$Gly^{280}$-[Tyr-Gln-Thr-Ile-End]-$Gly^{281}$: 5'-ccagcttttcttctg[ctagatggtctgata]cccacaccttctcct3'
$Val^{345}$-[Gly-Tyr-Gln-Thr-Ile]-$End^{346}$: 5'-atggcgtagggcacta[gatggtctgatagcc]caccccaatcttcat-3'

Mutants were subcloned from M13 vectors back into PcDNA I using the original restriction sites. All mutants were confirmed by dideoxy sequencing (Sanger, et al., *Proc. Natl. Acad. Sci. USA*, 74:5463, 1977) of the mutated region (Sequenase Kit Version 2.0, United States Biochemical).

Figure 2B:
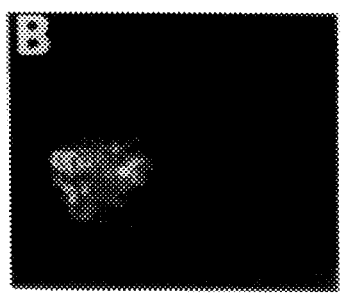
FIG. 2B shows cells transfected with modified mouse CD44 cDNA having a truncated cytoplasmic tail ending in the sequence Tyr-Gln-Thr-Ile-COOH, visualized with anti-mouse CD44 antibodies.
Figure 2C:
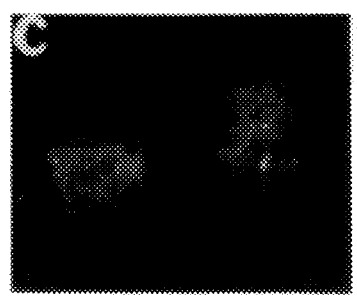
FIG. 2C shows cells transfected with modified mouse CD44 cDNA having a truncated cytoplasmic tail ending in the sequence Tyr-Gln-Thr-Ile-COOH, visualized with anti-human-LAMP-1 antibodies (on the right, outside the plane of focus is an untransfected cell).

The transfection and immunofluorescence procedures were identical to those in experiments described above except that murine LAMP-1 cDNA and the anti-murine LAMP-1 monoclonal antibody were substituted with murine CD44 cDNA and anti-murine CD44 monoclonal antibody. Cells transfected with CD44 were incubated with 0.7 ml of 50% rat anti-CD44 monoclonal antibody (that percentage being composed of an equal mixture of three individual monoclonal antibodies: LM33, H63, and 5D2-27, (Hughes, et al., *J. Biol. Chem.*, 258:1014, 1983), 50% H5G11, and 0.1% saponin for 30 min. Following transfection of human fibroblasts, the resulting protein was targeted to lysosomes (FIG. 2B) as indicated by co-localization with the lysosomal marker, human LAMP-1 (FIG. 2C, see cell at left side of panel).

Figure 2D:
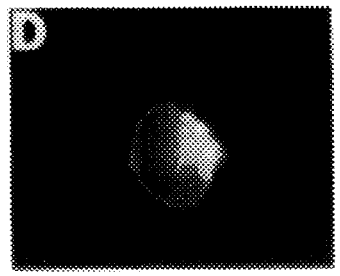
FIG. 2D shows cells transfected with modified mouse CD44 cDNA having the sequence Tyr-Gln-Thr-Ile-COOH at an internal position is the cytoplasmic tail, visualized with anti-mouse CD44 antibodies.
Figure 2E:
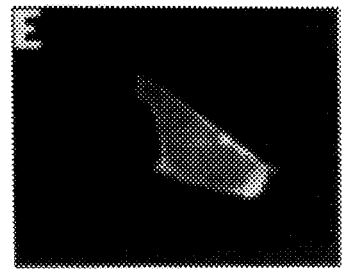
FIG. 2E shows cells transfected with modified mouse CD44 cDNA having the sequence Tyr-Gln-Thr-Ile-COOH after the carboxy terminus of the normal (non-truncated) CD44 cytoplasmic tail, visualized with anti-mouse CD44 antibodies.

Additional constructs indicated that the Tyr-Gln-Thr-Ile sequence, while sufficient to confer lysosomal membrane targeting, must occur in a specific context to mediate lysosomal signalling. Nontruncated mutant murine CD44 proteins having the sequence Tyr-Gln-Thr-Ile inserted between $Gly^{280}$ and $Gly^{281}$ (note that the stop codon is lacking, FIG. 2D) or having the motif placed after $Val^{345}$ (FIG. 2E), the carboxyl-terminal amino acid of murine CD44, were not targeted to lysosomes, but rather were visualized on the plasma membrane. Again, there was no nonspecific staining of the cells (FIGS. 2B and C, see the untransfected cell that is visible on the right side of panel C but not visible in panel B). As expected, unmodified transfected murine CD44 was directed to the plasma membrane (FIG. 2A).

Example 4

Identification of a Modification of the Cytoplasmic Tail of LAMP-1

To further elucidate the role of the cytoplasmic tail of LAMP-1 in the trafficking of the protein to the lysosomes, the proteolytic fragment corresponding to the cytoplasmic tail was isolated and sequenced. LAMP-1 was purified by ID4B monoclonal antibody affinity chromatography from a detergent extract made from the livers of Swiss Webster mice (Rockland). Frozen tissue was thawed in PBS, 1 mM phenylmethylsulfonyl fluoride (FMSF), and 1 mg/l aprotinin, and was disrupted with a polytron. The nuclear fraction pellet, obtained by centrifugation at 300×g for 10 min, was discarded. Membranes were collected by centrifugation at 50,000×g for 30 min. The pellet was resuspended in 10 mM Tris-HCl (pH 7.5), 1M guanidine HCl, 1 mM PMSF, and 1 mg/l aprotinin. The homogenate was spun at 50,000×g for 30 min and the pellet was resuspended in 1M KI, 10 mM tris HCl (pH 7.5), 1 mM PMSF, and 1 mg/l aprotinin. The homogenate was spun at 50,000×g for 30 min and the pellet was resuspended in 1% Triton X-100, 10 mM Tris HCl (pH 7.6), 0.4M KCl, 1 mM PMSF, and 1 mg/l aprotinin. The extract was subjected to quick freeze and thaw three times and dialyzed against 50 mM Tris HCL (pH 7.6), 0.2% Triton X-100, and 1 mM disodium ethylenedinitrilotetraacedic acid (EDTA). After centrifugation at 100,000×g for 1 hr the supernatant was placed over the antibody column equilibrated in the same buffer. Prior to elution of the protein, the column was exchanged into 50 mM Tris HCl (pH 7.5) containing 0.5% octyl glucoside, and washed with 10 column volumes of high salt buffer (1M NaCl, 100 mM boric acid, 25 mM sodium borate, pH 8.8). The protein was eluted with 100 mM diethylamine (pH 10.5) and 0.5% octyl glucoside into 0.12 volume of 2M Tris HCl (pH 7.5). Fractions containing the purified protein were pooled and concentrated to 2 to 3 mg/ml by negative pressure dialysis against 5 mM $NaPO_4$ (pH 7.4) containing 1 mM EDTA and 0.25% octyl glucoside.

Trifluoromethane sulfonic acid mediated deglycosylation, trypsin digestion, reverse phase chromatography, and amino acid sequence analysis were performed as described (Arterburn, et al., *J. Biol. Chem.*, 265:7419, 1990). Tryptic fragments were generated from both deglycosylated and native LAMP-1 protein purified from the membrane fraction of mouse livers by monoclonal antibody affinity chromatography. Peptides corresponding to the carboxyl terminal cytoplasmic tail were isolated by reverse phase chromatography and characterized by amino acid sequence analysis. According to the nucleotide sequence of murine LAMP-1 cDNA, a predicted tryptic cleavage after $Arg^{374}$ would yield the octomeric peptide $Ser^{375}$-$His^{376}$-$Ala^{377}$-$Gly^{378}$-$Tyr^{379}$-$Gln^{380}$-$Thr^{381}$-$Ile^{382}$, corresponding to the carboxyl terminus of the protein. However, the sequence of the tryptic peptide isolated from deglycolsylated LAMP-1 was the hexamer $Ser^{375}$-$His^{376}$-$Ala^{377}$-$Gly^{378}$-$Tyr^{379}$-$Gln^{380}$, which lacked the terminal Thr and Ile residues. This hexamer eluted with a retention time of 30 min. The same truncated peptide was obtained when the experiments were repeated with the native (non-deglycosylated) protein.

The possibility that the Thr and Ile residues were cleaved during the tryptic digestion procedures was examined by constructing a synthetic peptide corresponding to the cytoplasmic tail.

The peptide, $NH_2$-Leu-Ile-Gly-Arg-Lys-Arg-Ser-His-Ala-Gly-Tyr-Gln-Thr-Ile-COOH, was synthesized on an Applied Biosystems 430A automated peptide synthesizer and cleaved from the resin with hydrofluoric acid by Multiple Peptide Systems, San Diego. Peptide sequences were confirmed by $NH_2$-terminal sequence analysis and purity assessed by reverse phase HPLC. This synthetic peptide was subjected to the identical deglycosylation and trypsin digestion procedures as the native protein but yielded the predicted octomeric tryptic peptide Ser-His-Ala-Gly-Tyr-Gln- Thr-Ile. The HPLC retention time of the octomer was 10 min greater than that of the hexamer, correlating with the presence of the hydrophobic Ile residue. No such peak, corresponding to the octomer, was detectable in the original tryptic digests of deglycosylated or native murine LAMP-1 protein.

Example 5

The Use of the Modified Influenza Hemagglutinin (HA)/LAMP Chimera, Targeted to Lysosomes, as a Means to Enhance the MHC Class II/Helper T Cell Response to These Proteins as Antigens The system utilized to evaluate the strategy for MHC class II restricted antigen presentation of chimeric proteins with the LAMP lysosomal targeting signal uses the model antigen, influenza hemagglutinin (HA). HA is known to contain a number of helper T cell epitopes in various strains of mice. In particular, the amino acid fragment 111–120 represents a major helper epitope restricted by the MHC class II element I-E$^d$ in strains of mice such as BALB/c and DBA-2.

The intraluminal H1 subunit of the influenza virus HA gene containing residues 111–120 was amplified by PCR, and the transmembrane domain and cytoplasmic tail of LAMP-1 was ligated to the carboxyl terminus (3') of this truncated HA. A second, similar, chimera was synthesized with the terminal four amino acids (i.e. the lysosomal membrane targeting signal) of the LAMP-1 cytoplasmic tail deleted. These two HA/LAMP-1 chimeras and the unmodified HA were subcloned into mammalian expression vectors containing a selectable maker (neomycin). In transfection and immunofluorescence experiments performed in fibroblasts, it was determined that the HA/LAMP chimera with the lysosomal targeting signal localized to lysosomes as expected whereas the control HA/LAMP chimera lacking the targeting sequence and unmodified HA localized to the cell membrane as predicted. Therefore, as shown in earlier studies, the splicing of the LAMP cytoplasmic portion onto this model antigen efficiently re-routes it away from the bulk flow pathway to the membrane and into the endosomal/lysosomal compartment.

Specific MHC class II restricted T cell responses to these HA-LAMP constructs were assayed using a T cell receptor transgenic mouse in which the rearranged α and β chains derived from a T cell clone specific for HA 111–120 plus I-E$^d$ have been inserted into the murine germ line. In these mice, roughly 20% of the CD4$^+$ T cells express the HA specific T cell receptor; therefore, naive lymph node or splenic lymphocyte populations will respond by lymphokine secretion and proliferation when presented with the HA 111–120 by APCs expressing I-E$^d$. The I-E$^d$+B-cell lymphoma, A20 was used as an antigen presenting cell. Previous work demonstrated that when lysates from tumor cells expressing HA were fed to A20 cells, the HA protein was taken up and processed by the A20 cells and presented to T cells from the HA specific transgenic mice. A20 cells were stably transfected with one of two constructs: (1) wild-type HA and (2) a chimeric construct containing the extracellular and transmembrane portion of HA spliced to the cytoplasmic portion of the LAMP-1 gene (HA/LAMP).

As shown in FIG. 3, when dose response curves were performed with varying numbers of the transduced A20 cells, there was enhanced stimulation of the HA specific T cells from the transgenic mouse by A20 transduced with the HA/LAMP chimera relative to the A20 transduced with the wild-type HA or A20 loaded extracellularly with HA containing cell lysates. In one experiment, at the lowest dose of stimulator cells (300 cells per well) the HA/LAMP transduced A20 cells continued to stimulate maximum levels of proliferation. In contrast, the A20 cells transduced with a wild-type HA were significantly below plateau level with dilutions beyond 1,000 cells per well. These data indicate that the specific targeting of antigens to the endosomal/lysosomal compartment by linking them to the cytoplasmic LAMP targeting sequence markedly enhances MHC class II presentation.

A repeat of the experiment with additional experimental points using fewer antigen presenting cells (APC) is shown in FIG. 4. The HA/LAMP construct again showed a higher stimulating effect.

The HA antigen of influenza virus is normally processed and presented in infected cells only in conjunction with the MHC I molecule in the cytotoxic T cell pathway. We have used the influenza virus HA antigen as one model system by which to demonstrate the directed targeting of a viral protein to lysosomes and to the MHC class II/helper T cell pathway.

We claim:

1. A composition for eliciting an immune response in an animal to an antigen, comprising an antigen presenting cell expressing:

(a) a chimeric DNA segment encoding (1) an N-terminal domain containing a sequence encoding at least one epitope of said antigen, (2) a transmembrane domain, and (3) a cytoplasmic domain containing an endosomal/lysosomal targeting signal comprising the tetrapeptide sequence Tyr-Xaa-Xaa-Xbb, wherein Xaa is any amino acid and Xbb is a hydrophobic amino acid, wherein said targeting signal directs a protein expressed from said DNA sequence to the endosomal/lysosomal compartment; and (b) a major histocompatibility (MHC) class II molecule.

2. The composition of claim 1 wherein said antigen is selected from the group consisting of proteins of bacteria, protozoa, fungi and viruses.

3. The composition of claim 1 wherein said antigen is a protein of HIV.

4. A method for eliciting an immune response in an animal to an antigen, comprising administering to said animal a cell population containing an antigen presenting cell (APC), wherein said cell, after administration, will express:

(a) a chimeric DNA segment encoding (1) an N-terminal domain containing a sequence encoding at least one epitope of said antigen, (2) a transmembrane domain, and (3) a cytoplasmic domain containing an endosomal/lysosomal targeting signal comprising the tetrapeptide sequence Tyr-Xaa-Xaa-Xbb, wherein Xaa is any amino acid and Xbb is a hydrophobic amino acid, wherein said targeting signal directs a protein expressed from said DNA sequence to the endosomal/lysosomal compartment; and (b) a major histocompatibility complex (MHC) class II molecule, said molecule being compatible with the MHC proteins of said animal.

5. A method according to claim 4 wherein said antigen is selected from the group consisting of proteins of bacteria, protozoa, fungi and viruses.

6. A method according to claim 4 wherein said antigen is a protein of HIV.

7. A composition for eliciting an immune response in an animal to an antigen, comprising a vector containing a chimeric DNA segment which encodes a protein containing (1) an N-terminal domain containing a sequence encoding at least one epitope of said antigen, (2) a transmembrane domain and (3) a cytoplasmic domain containing an endosomal/lysosomal targeting signal comprising the tetrapeptide sequence Tyr-Xaa-Xaa-Xbb, wherein Xaa is any amino acid and Xbb is a hydrophobic amino acid, wherein said targeting signal directs the protein to the endosomal/lysosomal compartment.

8. The composition of claim 7, wherein the vector is a virus.

9. The composition of claim 7, wherein the animal is a human.

10. The composition of claim 7, wherein said antigen is selected from the group consisting of proteins of bacteria, protozoa, fungi and viruses.

11. The composition of claim 7 wherein said antigen is a protein of HIV.

12. A construct for eliciting an immune response in an animal to an antigen, comprising a chimeric DNA segment which encodes a protein containing (1) an N-terminal domain containing a sequence encoding at least one epitope of said antigen, (2) a transmembrane domain and (3) a cytoplasmic domain containing an endosomal/lysosomal targeting signal comprising the tetrapeptide sequence Tyr-Xaa-Xaa-Xbb, wherein Xaa is any amino acid and Xbb is a hydrophobic amino acid, wherein said targeting signal directs the protein to the endosomal/lysosomal compartment.

13. The construct of claim 12, wherein said antigen is selected from the group consisting of proteins of bacteria, protozoa, fungi, and viruses.

14. The construct of claim 12 wherein said antigen is a protein of HIV.

15. A method for eliciting an immune response to an antigen, comprising administering to an animal composition containing a vector infectious for said animal, wherein said vector contains a chimeric DNA segment which encodes a protein containing (1) an N-terminal domain containing at least one epitope of said antigen, (2) a transmembrane domain and (3) a cytoplasmic domain containing an endosomal/lysosomal targeting signal comprising the tetrapeptide sequence Tyr-Xaa-Xaa-Xbb, wherein Xaa is any amino acid and Xbb is a hydrophobic amino acid, wherein said targeting signal directs the protein expressed from said DNA to the endosomal/lysosomal compartment.

16. A method according to claim 15 wherein said antigen is selected from the group consisting of proteins of bacteria, protozoa, fungi and viruses.

17. A method according to claim 15 wherein said antigen is a protein of HIV.

18. In a method of treatment for a cancer patient, the improvement wherein a cell population is administered to said patient, said cell population containing an antigen presenting cell capable of replicating in said patient, wherein said cell, after administration, will express:

(a) a chimeric DNA segment encoding an N-terminal domain containing a sequence encoding at least one epitope of said protein, a transmembrane domain and a cytoplasmic domain containing an endosomal/lysosomal targeting signal comprising the tetrapeptide sequence Tyr-Xaa-Xaa-Xbb, wherein Xaa is any amino acid and Xbb is a hydrophobic amino acid, wherein said targeting signal directs a protein expressed from said DNA sequence to the endosomal/lysosomal compartment; and (b) a major histocompatibility complex (MHC) class II molecule, said molecule being compatible with the MHC proteins of said patient.

19. In a method of treatment for a cancer patient after resection of a neoplastic tumor, the improvement comprising the steps of:

(a) obtaining from said patient a cell population containing stem cells capable of differentiation into antigen presenting cells (APC);

(b) introducing into said stem cells a chimeric DNA segment which encodes a protein containing (1) an N-terminal domain containing at least one epitope of an antigen characteristically found on the cell surface of cells from the patient's tumor, (2) a transmembrane domain and (3) a cytoplasmic domain containing an endosomal/lysosomal targeting signal comprising the tetrapeptide sequence Tyr-Xaa-Xaa-Xbb, wherein Xaa is any amino acid and Xbb is a hydrophobic amino acid, wherein said targeting signal directs the protein to the endosomal/lysosomal compartment;

(c) administering to said patient said stem cells containing said chimeric DNA segment;

wherein said chimeric DNA segment is expressed by APC which also express MHC class II molecules and wherein said APC arise from differentiation of said stem cells.

20. The composition of claim 1 wherein the antigen presenting cell does not express any co-stimulatory signals and the antigen is an auto-antigen.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
      ( A ) LENGTH: 11 amino acids
      ( B ) TYPE: amino acid
      ( D ) TOPOLOGY: unknown ( i i ) MOLECULE TYPE: peptide ( i i i ) HYPOTHETICAL: NO ( v ) FRAGMENT TYPE: C-terminal ( v i ) ORIGINAL SOURCE:
      ( A ) ORGANISM: Homo sapiens ( x i ) SEQUENCE DESCRIPTION: SEQ ID NO:1:

Arg Lys Arg Ser His Ala Gly Tyr Gln Thr Ile
1               5                       10

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( v i ) ORIGINAL SOURCE:
        ( A ) ORGANISM: Homo sapiens ( x i ) SEQUENCE DESCRIPTION: SEQ ID NO:2:

Tyr Xaa Xaa Xaa
1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( v ) FRAGMENT TYPE: C-terminal ( v i ) ORIGINAL SOURCE:
        ( A ) ORGANISM: Homo sapiens ( x i ) SEQUENCE DESCRIPTION: SEQ ID NO:3:

Tyr Gln Thr Ile
1

( 2 ) INFORMATION FOR SEQ ID NO:4:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: YES ( v i ) ORIGINAL SOURCE:
        ( A ) ORGANISM: Homo sapiens ( x i ) SEQUENCE DESCRIPTION: SEQ ID NO:4:

CTCTAGACTC GAGGCTAGCC GGCGTGACTC CTCT        34

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: YES (vi) ORIGINAL SOURCE:
    (A) ORGANISM: Homo sapiens (xi) SEQUENCE DESCRIPTION: SEQ ID NO:5:

CTCTAGACTC GAGGCTAATA GCCGGCGTGA CTCC         34

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: YES (vi) ORIGINAL SOURCE:
        (A) ORGANISM: Homo sapiens (xi) SEQUENCE DESCRIPTION: SEQ ID NO:6:

CTCTAGACTC GAGGCTACTG ATAGCCGGCG TGA          33

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: YES (vi) ORIGINAL SOURCE:
        (A) ORGANISM: Homo sapiens (xi) SEQUENCE DESCRIPTION: SEQ ID NO:7:

CTCTAGACTC GAGGCTAGGT CTGATAGCCG GCGT         34

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: cDNA (iii) HYPOTHETICAL: YES (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 4..15

(xi) SEQUENCE DESCRIPTION: SEQ ID NO:8:

GGC TAT CAG ACC CTC TAG                      18
    Tyr Gln Thr Leu
    1

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

Tyr Gln Thr Leu
 1

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 4..15

( x i ) SEQUENCE DESCRIPTION: SEQ ID NO:10:

GGC TAT CAG ACC TTC TAG        18
    Tyr Gln Thr Phe
     1

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

Tyr Gln Thr Phe
 1

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 3..14

( x i ) SEQUENCE DESCRIPTION: SEQ ID NO:12:

GC TAT CAG ACC ACC TAGC                                    18

Tyr Gln Thr Thr
    1

( 2 ) INFORMATION FOR SEQ ID NO:13:

( i ) SEQUENCE CHARACTERISTICS:
                 ( A ) LENGTH: 4 amino acids
                 ( B ) TYPE: amino acid
                 ( D ) TOPOLOGY: linear ( i i ) MOLECULE TYPE: protein ( x i ) SEQUENCE DESCRIPTION: SEQ ID NO:13:

Tyr Gln Thr Thr
 1

( 2 ) INFORMATION FOR SEQ ID NO:14:

( i ) SEQUENCE CHARACTERISTICS:
                 ( A ) LENGTH: 22 base pairs
                 ( B ) TYPE: nucleic acid
                 ( C ) STRANDEDNESS: double
                 ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
                 ( A ) ORGANISM: Homo sapiens ( i x ) FEATURE:
                 ( A ) NAME/KEY: CDS
                 ( B ) LOCATION: 8..19

( x i ) SEQUENCE DESCRIPTION: SEQ ID NO:14:

CGCCGGC TAT GCG ACC ATC TAG                                22

Tyr Ala Thr Ile
         1

( 2 ) INFORMATION FOR SEQ ID NO:15:

( i ) SEQUENCE CHARACTERISTICS:
                 ( A ) LENGTH: 4 amino acids
                 ( B ) TYPE: amino acid
                 ( D ) TOPOLOGY: linear ( i i ) MOLECULE TYPE: protein ( x i ) SEQUENCE DESCRIPTION: SEQ ID NO:15:

Tyr Ala Thr Ile
 1

( 2 ) INFORMATION FOR SEQ ID NO:16:

( i ) SEQUENCE CHARACTERISTICS:
                 ( A ) LENGTH: 21 base pairs
                 ( B ) TYPE: nucleic acid
                 ( C ) STRANDEDNESS: double
                 ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
     ( A ) ORGANISM: Homo sapiens ( i x ) FEATURE:
     ( A ) NAME/KEY: CDS
     ( B ) LOCATION: 5..16

( x i ) SEQUENCE DESCRIPTION: SEQ ID NO:16:

CGGC TAT CAG GCC ATC TAGCC          21

Tyr Gln Ala Ile
      1

( 2 ) INFORMATION FOR SEQ ID NO:17:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: protein ( x i ) SEQUENCE DESCRIPTION: SEQ ID NO:17:

Tyr Gln Ala Ile
 1

( 2 ) INFORMATION FOR SEQ ID NO:18:

( i ) SEQUENCE CHARACTERISTICS:
          ( A ) LENGTH: 28 base pairs
          ( B ) TYPE: nucleic acid
          ( C ) STRANDEDNESS: double
          ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
          ( A ) ORGANISM: Homo sapiens ( i x ) FEATURE:
          ( A ) NAME/KEY: CDS
          ( B ) LOCATION: 10..21

( x i ) SEQUENCE DESCRIPTION: SEQ ID NO:18:

CACGCCGGC TAT GCG GCC ATC TAGCCTG          28

Tyr Ala Ala Ile
           1

( 2 ) INFORMATION FOR SEQ ID NO:19:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: protein ( x i ) SEQUENCE DESCRIPTION: SEQ ID NO:19:

Tyr Ala Ala Ile
 1

( 2 ) INFORMATION FOR SEQ ID NO:20:

( i ) SEQUENCE CHARACTERISTICS:
          ( A ) LENGTH: 43 base pairs
          ( B ) TYPE: nucleic acid ( C ) STRANDEDNESS: double
                    ( D ) TOPOLOGY: linear ( i i ) MOLECULE TYPE: cDNA ( i i i ) HYPOTHETICAL: YES ( i v ) ANTI-SENSE: YES ( v i ) ORIGINAL SOURCE:
                    ( A ) ORGANISM: Homo sapiens ( x i ) SEQUENCE DESCRIPTION: SEQ ID NO:20:

CCAGCTTTTT CTTCTGGATG GTCTGATACC CACACCTTCT CCT 43

( 2 ) INFORMATION FOR SEQ ID NO:21:

( i ) SEQUENCE CHARACTERISTICS:
                    ( A ) LENGTH: 6 amino acids
                    ( B ) TYPE: amino acid
                    ( D ) TOPOLOGY: unknown ( i i ) MOLECULE TYPE: peptide ( i i i ) HYPOTHETICAL: YES ( v ) FRAGMENT TYPE: internal ( v i ) ORIGINAL SOURCE:
                    ( A ) ORGANISM: Homo sapiens ( x i ) SEQUENCE DESCRIPTION: SEQ ID NO:21:

Gly Tyr Gln Thr Ile Gly
 1               5

( 2 ) INFORMATION FOR SEQ ID NO:22:

( i ) SEQUENCE CHARACTERISTICS:
                    ( A ) LENGTH: 46 base pairs
                    ( B ) TYPE: nucleic acid
                    ( C ) STRANDEDNESS: double
                    ( D ) TOPOLOGY: linear ( i i ) MOLECULE TYPE: cDNA ( i i i ) HYPOTHETICAL: YES ( i v ) ANTI-SENSE: YES ( v i ) ORIGINAL SOURCE:
                    ( A ) ORGANISM: Homo sapiens ( x i ) SEQUENCE DESCRIPTION: SEQ ID NO:22:

CCAGCTTTTT CTTCTGCTAG ATGGTCTGAT ACCCACACCT TCTCCT 46

( 2 ) INFORMATION FOR SEQ ID NO:23:

( i ) SEQUENCE CHARACTERISTICS:
                    ( A ) LENGTH: 5 amino acids
                    ( B ) TYPE: amino acid
                    ( D ) TOPOLOGY: unknown ( i i ) MOLECULE TYPE: peptide ( i i i ) HYPOTHETICAL: YES ( v ) FRAGMENT TYPE: C-terminal ( v i ) ORIGINAL SOURCE:
                    ( A ) ORGANISM: Homo sapiens ( x i ) SEQUENCE DESCRIPTION: SEQ ID NO:23:

Gly Tyr Gln Thr Ile (2) INFORMATION FOR SEQ ID NO:24:

(i) SEQUENCE CHARACTERISTICS:
    (A) LENGTH: 46 base pairs
    (B) TYPE: nucleic acid
    (C) STRANDEDNESS: double
    (D) TOPOLOGY: linear (ii) MOLECULE TYPE: cDNA (iii) HYPOTHETICAL: YES (iv) ANTI-SENSE: YES (vi) ORIGINAL SOURCE:
    (A) ORGANISM: Homo sapiens (xi) SEQUENCE DESCRIPTION: SEQ ID NO:24:

ATGGCGTAGG GCACTAGATG GTCTGATAGC CCACCCCAAT CTTCAT          46

(2) INFORMATION FOR SEQ ID NO:25:

(i) SEQUENCE CHARACTERISTICS:
    (A) LENGTH: 6 amino acids
    (B) TYPE: amino acid
    (D) TOPOLOGY: unknown (ii) MOLECULE TYPE: peptide (iii) HYPOTHETICAL: YES (v) FRAGMENT TYPE: C-terminal (vi) ORIGINAL SOURCE:
    (A) ORGANISM: Homo sapiens (xi) SEQUENCE DESCRIPTION: SEQ ID NO:25:

Val Gly Tyr Gln Thr Ile
  1               5

(2) INFORMATION FOR SEQ ID NO:26:

(i) SEQUENCE CHARACTERISTICS:
    (A) LENGTH: 8 amino acids
    (B) TYPE: amino acid
    (D) TOPOLOGY: unknown (ii) MOLECULE TYPE: peptide (iii) HYPOTHETICAL: NO (iv) ANTI-SENSE: NO (v) FRAGMENT TYPE: C-terminal (vi) ORIGINAL SOURCE:
    (A) ORGANISM: Homo sapiens (xi) SEQUENCE DESCRIPTION: SEQ ID NO:26:

Ser His Ala Gly Tyr Gln Thr Ile
  1               5

(2) INFORMATION FOR SEQ ID NO:27:

(i) SEQUENCE CHARACTERISTICS:
    (A) LENGTH: 6 amino acids
    (B) TYPE: amino acid
    (D) TOPOLOGY: unknown (ii) MOLECULE TYPE: peptide -continued (iii) HYPOTHETICAL: YES (v) FRAGMENT TYPE: C-terminal (vi) ORIGINAL SOURCE:
    (A) ORGANISM: Homo sapiens (xi) SEQUENCE DESCRIPTION: SEQ ID NO:27:

Ser His Ala Gly Tyr Gln
1               5

(2) INFORMATION FOR SEQ ID NO:28:

(i) SEQUENCE CHARACTERISTICS:
       (A) LENGTH: 14 amino acids
       (B) TYPE: amino acid
       (D) TOPOLOGY: unknown (ii) MOLECULE TYPE: peptide (iii) HYPOTHETICAL: YES (v) FRAGMENT TYPE: C-terminal (vi) ORIGINAL SOURCE:
       (A) ORGANISM: homo sapiens (xi) SEQUENCE DESCRIPTION: SEQ ID NO:28:

Leu Ile Gly Arg Lys Arg Ser His Ala Gly Tyr Gln Thr Ile
1               5                       10